(12) United States Patent
Butler et al.

(10) Patent No.: US 9,277,908 B2
(45) Date of Patent: *Mar. 8, 2016

(54) RETRACTOR

(71) Applicant: Atropos Limited, County Wicklow (IE)

(72) Inventors: John Butler, County Mayo (IE); Derek William Young, County Dublin (IE); Aoibheann Gill, County Longford (IE); Alan Reid, Dublin (IE); Frank Bonadio, County Wicklow (IE)

(73) Assignee: Atropos Limited, Bray, County Wicklow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,159

(22) Filed: Feb. 27, 2015

(65) Prior Publication Data

US 2015/0272563 A1 Oct. 1, 2015

Related U.S. Application Data

(63) Continuation of application No. 13/205,517, filed on Aug. 8, 2011, now Pat. No. 8,986,202, which is a continuation of application No. 11/841,777, filed on Aug. 20, 2007, now Pat. No. 8,012,088, which is a (Continued)

(30) Foreign Application Priority Data

Oct. 14, 1999 (IE) .......................................... 990861
Dec. 16, 1999 (IE) .......................................... 991053
Feb. 18, 2000 (EP) ..................................... 00650010

(51) Int. Cl.
*A61B 17/02* (2006.01)
*A61B 1/32* (2006.01)
(Continued)

(52) U.S. Cl.
CPC ............... *A61B 17/0218* (2013.01); *A61B 1/32* (2013.01); *A61B 17/0206* (2013.01);
(Continued)

(58) Field of Classification Search
CPC .. A61B 1/32; A61B 17/0293; A61B 17/3423; A61B 17/3421; A61B 17/3431
See application file for complete search history.

(56) References Cited

U.S. PATENT DOCUMENTS

| 1,157,202 A | 10/1915 | McLeland |
| 1,598,284 A | 8/1926 | Kinney |

(Continued)

FOREIGN PATENT DOCUMENTS

| DE | 37 39 532 | 12/1988 |
| DE | 37 37 121 | 5/1989 |

(Continued)

OTHER PUBLICATIONS

Kagaya, "Laparoscopic cholecystectomy via two ports, using the 'Twin-Port' system", J. Hepatobiliary Pancreat Surg (2001) 8:76-80.

*Primary Examiner* — Anu Ramana
(74) *Attorney, Agent, or Firm* — Bookoff McAndrews, PLLC

(57) ABSTRACT

A retractor (101) for retracting the margins of a wound opening (103) comprises an inner anchoring O-ring (105) attached to a cylindrical sleeve (106) at a distal end and a reinforcing O-ring (109) attached to a proximal end of the sleeve (106). The sleeve (106) is led between an inner ring part (110) and a corresponding recess (116) in an outer ring part (111). The outer ring part (111) has anchor formations (120) over which the proximal end of the sleeve (106) is attached to anchor the sleeve (106). To retract the wound opening (103) the sleeve (106) is pulled while the guide rings (110, 111) are moved against the tissue surrounding the wound opening (103). This pulls the inner O-ring (105) against the inside of the tissue adjacent the wound opening (103), and retracts the wound opening (103). The sleeve (106) is manipulated locally for maximum retraction efficiency.

20 Claims, 24 Drawing Sheets

Related U.S. Application Data continuation of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534.

(51) Int. Cl.
*A61B 19/00* (2006.01)
*A61B 17/34* (2006.01)
*A61B 17/00* (2006.01)

(52) U.S. Cl.
CPC ........ *A61B 17/0293* (2013.01); *A61B 17/3423* (2013.01); *A61B 19/26* (2013.01); *A61B 17/3421* (2013.01); *A61B 17/3431* (2013.01); *A61B 2017/00557* (2013.01); *A61B 2017/0225* (2013.01); *A61B 2017/3429* (2013.01); *A61B 2017/3488* (2013.01); *A61B 2017/3492* (2013.01)

(56) References Cited

U.S. PATENT DOCUMENTS

| | | |
|---|---|---|
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,002,557 A | 3/1991 | Hasson |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |

(56) References Cited

U.S. PATENT DOCUMENTS

| | | |
|---|---|---|
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,582,577 A | 12/1996 | Lund et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroeck |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,769,783 A | 6/1998 | Fowler |
| 5,769,794 A | 6/1998 | Conlan et al. |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Mueller, Jr. et al. |
| 5,832,925 A | 11/1998 | Rothrum |
| 5,848,992 A | 12/1998 | Hart et al. |
| 5,853,395 A | 12/1998 | Crook et al. |
| 5,865,728 A | 2/1999 | Moll et al. |
| 5,871,474 A | 2/1999 | Hermann et al. |
| 5,882,344 A | 3/1999 | Strouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,036,685 A | 3/2000 | Mueller |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,328,730 B1 | 12/2001 | Harkrider, Jr. |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,485,467 B1 | 11/2002 | Crook et al. |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,569,119 B1 | 5/2003 | Haberland et al. |
| 6,578,577 B2 | 6/2003 | Bonadio et al. |
| 6,582,364 B2 | 6/2003 | Butler et al. |

(56) References Cited

U.S. PATENT DOCUMENTS

| | | |
|---|---|---|
| 6,589,167 B1 | 7/2003 | Shimonmura |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |
| 6,793,621 B2 | 9/2004 | Butler et al. |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Byordi |
| 7,008,377 B2 | 3/2006 | Beane |
| 7,052,454 B2 | 5/2006 | Taylor |
| 7,081,089 B2 | 7/2006 | Bonadio et al. |
| 7,083,626 B2 | 8/2006 | Hart et al. |
| 7,112,185 B2 | 9/2006 | Hart et al. |
| 7,118,528 B1 | 10/2006 | Piskun |
| 7,153,319 B1 | 12/2006 | Haberland et al. |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,749,415 B2 | 7/2010 | Brustad et al. |
| 7,753,901 B2 | 7/2010 | Piskun et al. |
| 7,837,612 B2 | 11/2010 | Gill et al. |
| 7,867,164 B2 | 1/2011 | Butler et al. |
| 7,909,760 B2 | 3/2011 | Albrecht et al. |
| 7,998,068 B2 | 8/2011 | Bonadio et al. |
| 8,012,088 B2 | 9/2011 | Butler et al. |
| 8,021,296 B2 | 9/2011 | Bonadio et al. |
| 8,157,817 B2 | 4/2012 | Bonadio et al. |
| 8,187,178 B2 | 5/2012 | Bonadio et al. |
| 8,317,691 B2 | 11/2012 | Bonadio et al. |
| 8,375,955 B2 | 2/2013 | Desai et al. |
| 8,518,024 B2 | 8/2013 | Williams et al. |
| 8,657,740 B2 | 2/2014 | Bonadio et al. |
| 8,734,336 B2 | 5/2014 | Bonadio et al. |
| 2001/0037053 A1 | 11/2001 | Bonadio et al. |
| 2001/0039430 A1 | 11/2001 | Dubrul et al. |
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0068232 A1 | 4/2004 | Hart et al. |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1 | 8/2004 | Bonadio et al. |
| 2004/0215063 A1 | 10/2004 | Bonadio et al. |
| 2004/0230161 A1 | 11/2004 | Zeiner |
| 2004/0249248 A1 | 12/2004 | Bonadio et al. |
| 2004/0260244 A1 | 12/2004 | Piechowicz et al. |
| 2005/0020884 A1 | 1/2005 | Heart et al. |
| 2005/0033246 A1 | 2/2005 | Ahlberg |
| 2005/0059865 A1 | 3/2005 | Kahle |
| 2005/0065475 A1 | 3/2005 | Hart et al. |
| 2005/0065543 A1 | 3/2005 | Kahle |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0267419 A1 | 12/2005 | Smith |
| 2005/0277946 A1 | 12/2005 | Greenhalgh |
| 2005/0288558 A1 | 12/2005 | Ewers |
| 2005/0288634 A1 | 12/2005 | O' Herron |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0106402 A1 | 5/2006 | McLucas |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0258899 A1 | 11/2006 | Gill et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0185387 A1 | 8/2007 | Albrecht et al. |
| 2007/0203398 A1 | 8/2007 | Bonadio et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0149714 A1 | 6/2009 | Bonadio |
| 2009/0187079 A1 | 7/2009 | Albrecht et al. |
| 2009/0292176 A1 | 11/2009 | Bonadio et al. |
| 2009/0326330 A1 | 12/2009 | Bonadio et al. |
| 2010/0057121 A1 | 3/2010 | Piskun et al. |
| 2010/0063362 A1 | 3/2010 | Bonadio et al. |

(56) References Cited

U.S. PATENT DOCUMENTS

| | | |
|---|---|---|
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0113886 A1 | 5/2010 | Piskun et al. |
| 2010/0204548 A1 | 8/2010 | Bonadio et al. |
| 2010/0217087 A1 | 8/2010 | Bonadio et al. |
| 2010/0274091 A1 | 10/2010 | Rothstein et al. |
| 2010/0274093 A1 | 10/2010 | Shelton, IV |
| 2010/0280326 A1 | 11/2010 | Hess et al. |
| 2011/0270195 A1 | 11/2011 | Piskun |
| 2012/0022333 A1 | 1/2012 | Main et al. |
| 2013/0245373 A1 | 9/2013 | Okoniewski |

FOREIGN PATENT DOCUMENTS

| | | |
|---|---|---|
| DE | 296 00 939 | 6/1998 |
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| EP | 1312318 | 5/2003 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-509659 | 4/2004 |
| JP | 2004-195037 | 7/2004 |
| RU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 01/91653 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2005/089661 | 9/2005 |
| WO | WO 2006/040748 A1 | 4/2006 |
| WO | WO 2006/059318 | 8/2006 |
| WO | WO 2008/121294 A1 | 10/2008 |
| WO | WO 2009/035663 A2 | 3/2009 |
| WO | WO 2014/144233 A1 | 9/2014 |

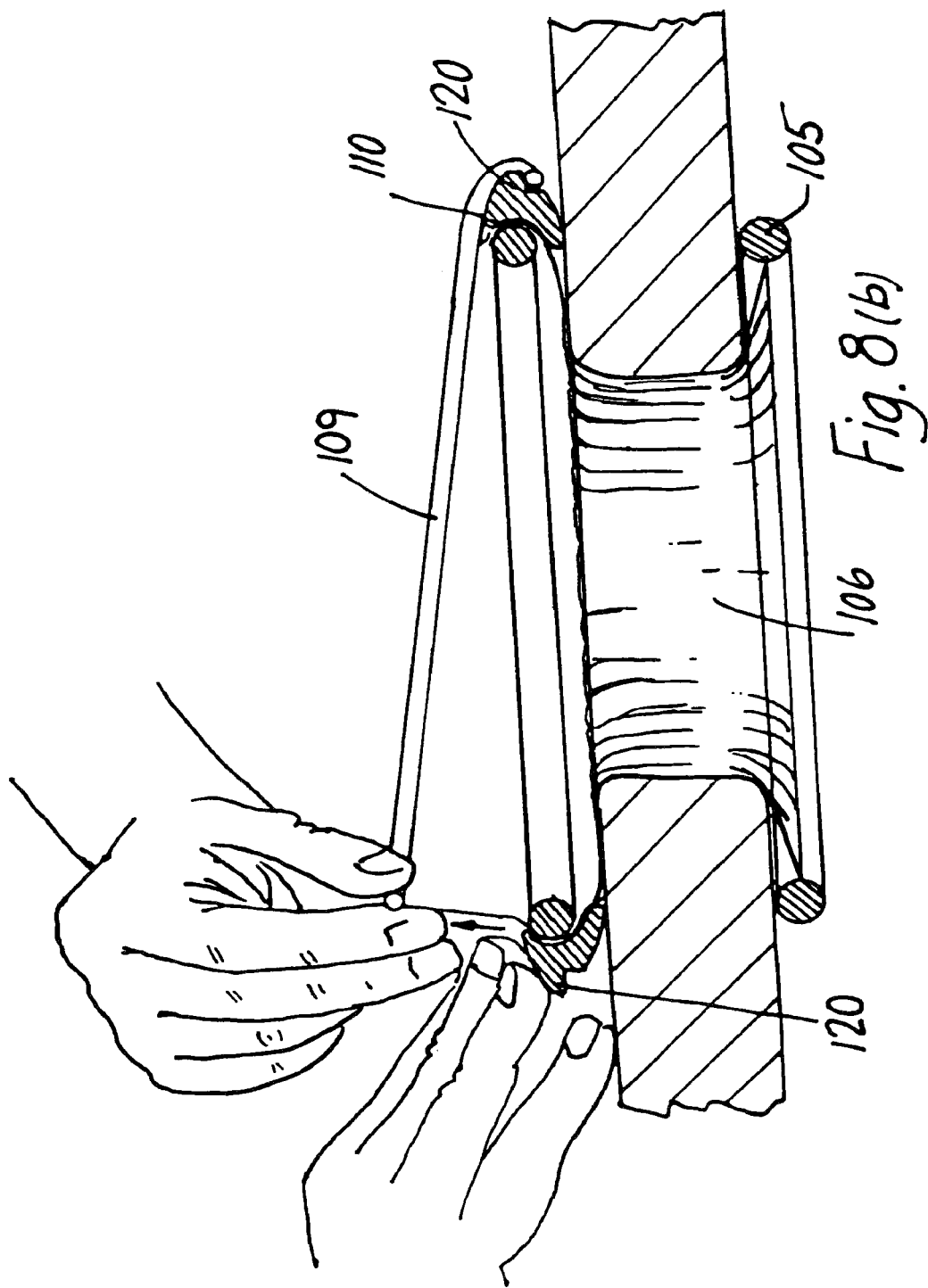

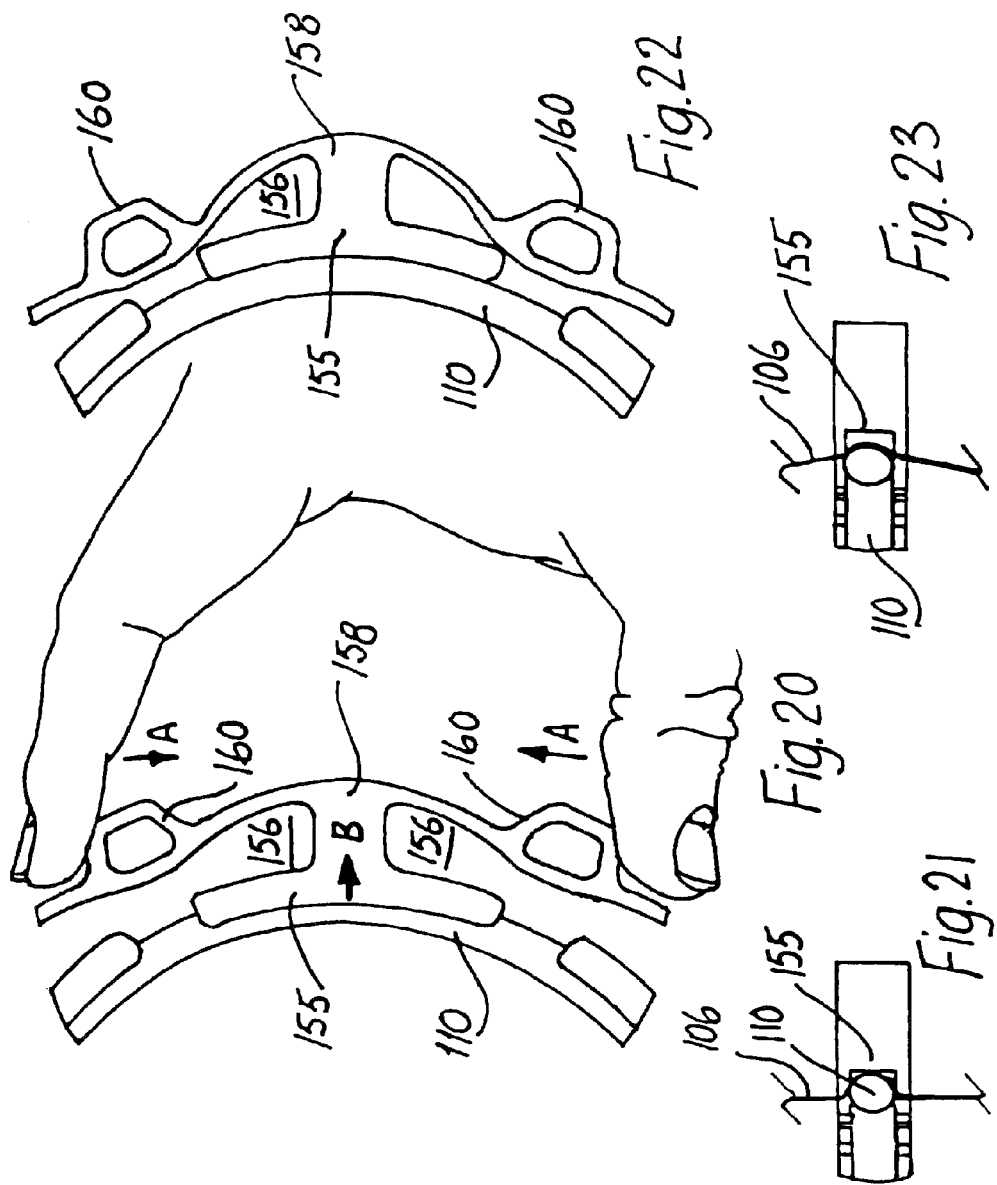

RETRACTOR

This application is a Continuation of Application Ser. No. 13/205,517, filed Aug. 8, 2011, now U.S. Pat. No. 8,986,202, which is a Continuation of Application Ser. No. 11/841,777, filed Aug. 20, 2007, now U.S. Pat. No. 8,012,088, which is a Continuation of Application Ser. No. 10/374,523, filed Feb. 27, 2003, Now U.S. Patent No. 7,445,597, which is a Continuation of Application Ser. No. 09/849,341, filed May 7, 2001, now U.S. Pat. No. 6,582,364, which is a Continuation of Application Ser. No. 09/688,138, filed Oct. 16, 2000, now U.S. Pat. No. 6,254,534, all of which are incorporated herein by reference in their entireties.

INTRODUCTION

The invention relates to a retractor. In particular the invention relates to a retractor for retracting the margins of an incision or a natural bodily orifice to provide maximum exposure of an organ or body structures for examination and/or access for surgical procedures, while also providing protection for the exposed sides of the incised tissue.

Various retractors are known. However in general known retractors are difficult and cumbersome to use, and/or are relatively expensive. In addition known retractors are limited to use with a particular size of incision and a particular patient anatomy.

This invention is directed towards providing an improved wound retractor which will overcome at least some of these problems, and in addition provide a means of wound protection during a surgical procedure.

STATEMENTS OF INVENTION

According to the invention there is provided a surgical wound retractor comprising:
  a distal anchoring member for insertion into a wound opening;
  a connecting means having an inner wound engaging portion and an outer portion, the wound engaging portion being mounted to the distal anchoring member, the connecting means having an insertion configuration in which the inner wound engaging portion has a reduced radial dimension and a retracting configuration;
  an external guide means for the outer portion of the connecting means;
  the external guide means being movable relative to the connecting means to shorten the axial extent of the connecting means and thereby bias the wound engaging portion of the connecting member into the retracting configuration to retract the wound opening laterally; and
  external anchoring means for anchoring the connecting means to maintain retraction of the opening.

In one preferred embodiment of the invention at least the inner wound engaging portion of the connecting means comprises a sleeve for extending around the wound opening to protect the opening.

In one embodiment the outer portion of the connecting means comprises a sleeve extension of the inner wound engaging portion of the connecting means.

Preferably the connecting means comprises a generally cylindrical sleeve.

In a preferred embodiment the guide means comprises an annular ring means. The annular ring means preferably comprises inner and outer ring parts between which the connecting means is led. In a preferred embodiment the outer ring part includes the anchor means for anchoring the connecting means. In one arrangement the anchor means comprises anchor formations on the outer ring to which the connecting means is attached on retraction of the opening.

Preferably the inner ring means defines a projection for location in a complementary recess of the outer ring with the connecting means located therebetween.

In one embodiment the inner ring is a relatively loose fit in the recess of the outer ring part.

Preferably at least portion of one of the ring parts is movable from a rest position in which the connecting member is substantially clamped between the ring parts to a release position in which at least portion of the connecting member is movable relative to the ring parts. Ideally only portion of the connecting member is movable relative to the ring parts in the release position.

In another embodiment the inner ring is a relatively tight fit in the outer ring part to grip the connecting member therebetween.

In one aspect of the invention the outer ring part comprises a plurality of interconnected segments which are independently movable to facilitate localised release of the connecting member for adjusting of the retraction force applied at the opening. The ring part or segment thereof is preferably manually manipulable between the clamped rest position and the release position.

In one embodiment of the invention the connecting means includes a proximal reinforcing means for engagement with the external anchoring means. Ideally the proximal reinforcing means is a proximal ring.

Preferably the distal anchoring means is of resilient material. Typically the distal anchoring means is an O-ring.

Preferably at least an outer surface of the guide means which engages with the connecting means is of a material with a low coefficient of friction such as polytetrafluroethylene.

In a particularly preferred embodiment the retractor includes a platform for attachment of another device to the retractor.

In an especially preferred arrangement one of the ring parts defines a platform for attachment of another device to the retractor.

In another aspect the invention provides a method for retracting a wound opening using a surgical wound retractor comprising a distal anchoring member, a connecting means having a wound engaging portion mounted to the distal anchoring member and an outer portion, an external guide means for the outer portion of the connecting means and an external anchoring means; the method comprising the steps:
  positioning the distal anchoring member to be retained inside a wound opening with the connecting means extending: outwardly therefrom through the opening;
  moving the external guide means relative to the outer portion of the connecting means to shorten the axial extent of the connecting means and thereby bias the wound engaging portion into a retracting configuration to retract the wound opening; and
  anchoring the connecting means to maintain retraction of the wound opening.

Preferably the method includes the steps of moving the external guide means relative to the outer portion of the connecting means to partially retract the wound opening, gripping the outer portion of the connecting means and pulling it relative to the guide means to fully retract the wound opening.

In one embodiment the method includes the steps of:
  (a) gripping a local section of the outer portion of the connecting means while the remaining section of the outer portion of the connecting means is anchored, (b) pulling the local section to increase the retraction at a local area of the wound opening, and (c) anchoring the local section of the connecting means.

Ideally the method includes repeating steps (a) to (c) for other local sections of the outer portion of the connecting means.

BRIEF DESCRIPTION OF THE DRAWINGS

The invention will be more clearly understood from the following description thereof given by way of example only with reference to the accompanying drawings, in which:

FIGS. 8(a) and 8(b) are side cross sectional views illustrating lateral retraction of the wound opening using the retractor of FIG. 2;

FIG. 20 is a schematic plan view illustrating manipulation of a part of the retractor of FIGS. 17 to 19;

FIG. 21 is a side cross sectional view of the retractor part in the configuration of FIG. 20;

FIG. 22 is a schematic plan view of the retractor part in a release position;

FIG. 23 is a side cross sectional view of the retractor part in the configuration of FIG. 22;

DETAILED DESCRIPTION

Figure 3:
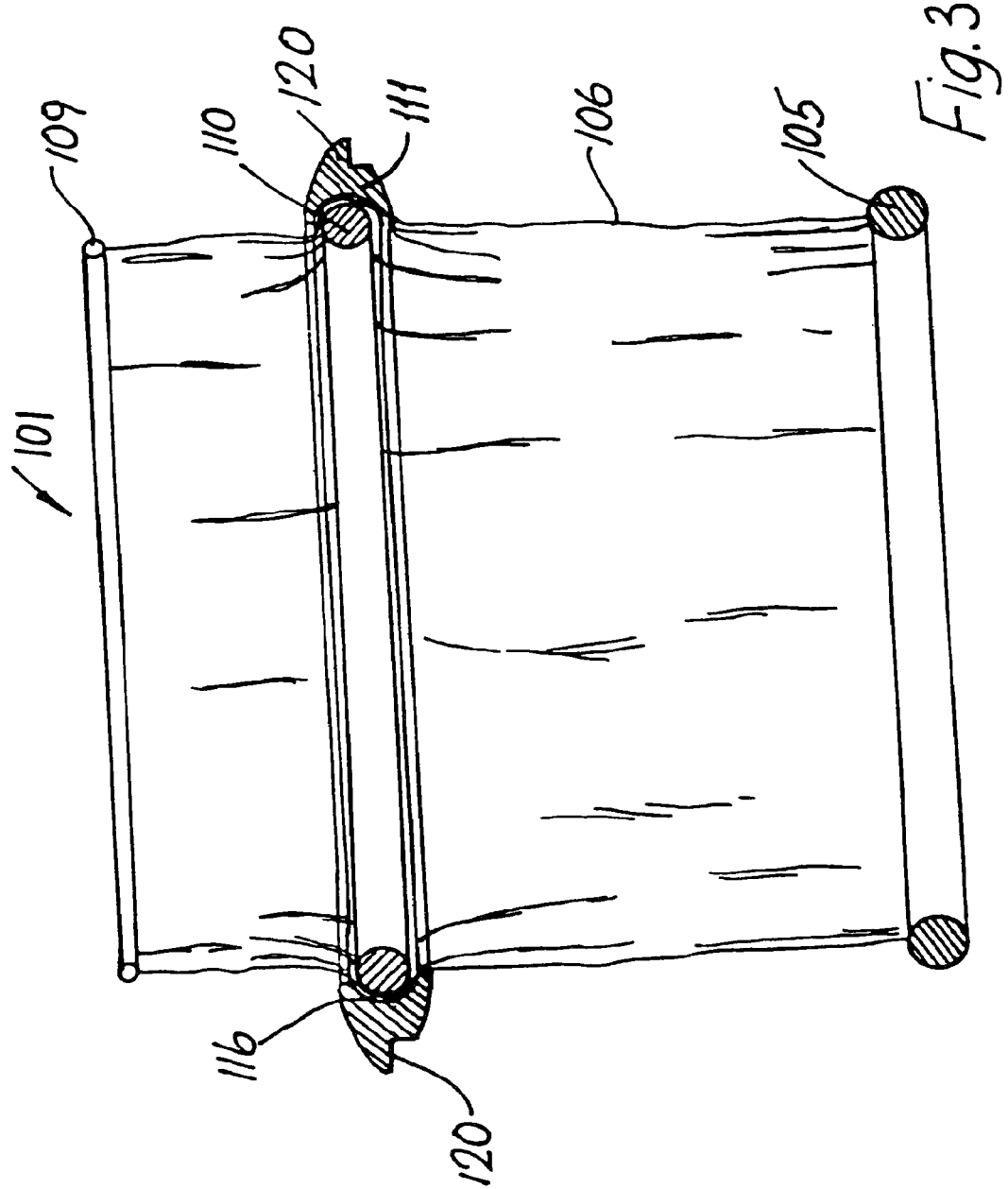
FIG. 3 is a side cross sectional view of the assembled retractor of FIG. 2.
Figure 4:
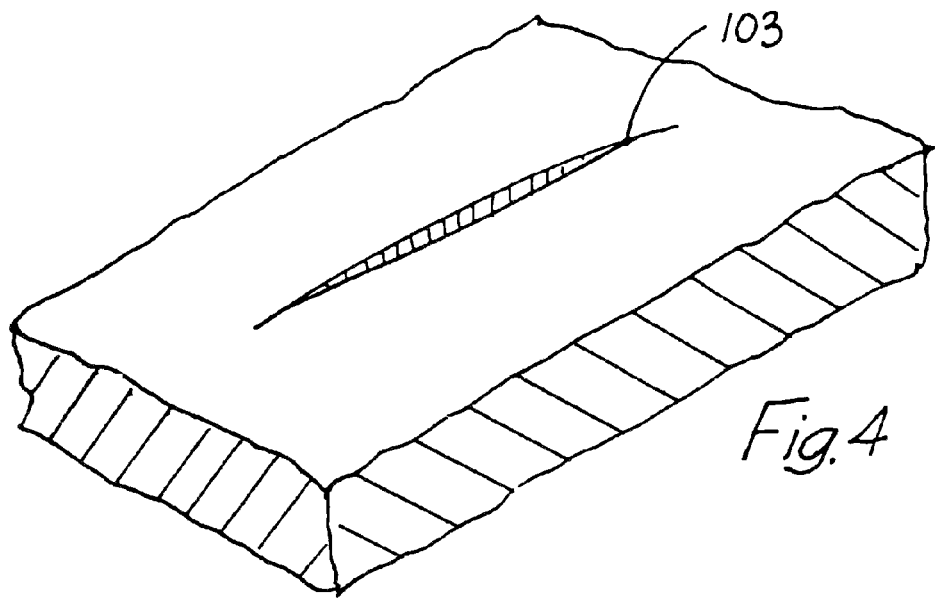
FIG. 4 is a perspective view of an unretracted wound opening.

Referring to FIGS. 1 to 13 there is illustrated a wound retractor 101 according to the invention, which in the case illustrated is used to retract the margins of a wound such as an abdominal wound opening 103, as illustrated in FIG. 4.

The reactor 101 comprises a distal anchoring member, in this case in the form of a resilient inner O-ring 105, for insertion into the wound opening 103, and a connecting means, in this case in the form of an elastomeric sleeve 106 which is substantially cylindrical. The sleeve 106 has an inner wound engaging portion and an outer portion, and the wound engaging portion is attached to the inner O-ring 105. The sleeve has an insertion configuration in which the inner wound engaging portion has a reduced radial dimension and a retracting configuration to retract the wound opening 103 laterally.

An external guide means is provided for the outer portion of the sleeve 106, and in this case the guide means comprises an inner ring part 110 and an outer ring part 111 between which the sleeve 106 is led. The retractor 101 includes external anchoring means for anchoring the sleeve 106 to maintain retraction of the wound opening 103, and in this case the anchoring means is provided by a plurality of anchor formations 120 on the outer surface of the outer ring part 111 (FIG. 2), the formations 120 extending radially outwardly to define hooks.

The outer ring part 111 is of the same annular shape as the inner ring part 110 but has a larger diameter and a recess 116. The inner ring part 110 is of a relatively stiff material and mates with the outer ring part 111 in the recess 116 to slidably retain the sleeve 106 therebetween, as illustrated in FIG. 3. In this case the ring parts 110, 111 are a relatively loose fit to facilitate movement of the ring parts 110, 111 relative to the sleeve 106 to shorten the axial extent of the sleeve 106 and thereby bias the wound engaging portion into the retracting configuration to retract the wound opening 103 laterally.

The ring parts 110, 111 are of a material with a low coefficient of friction such as Polytetrafluoroethylene (PTFE). PTFE is a tough, non-resilient material of moderate tensile strength and with excellent lubricity.

Figure 1:
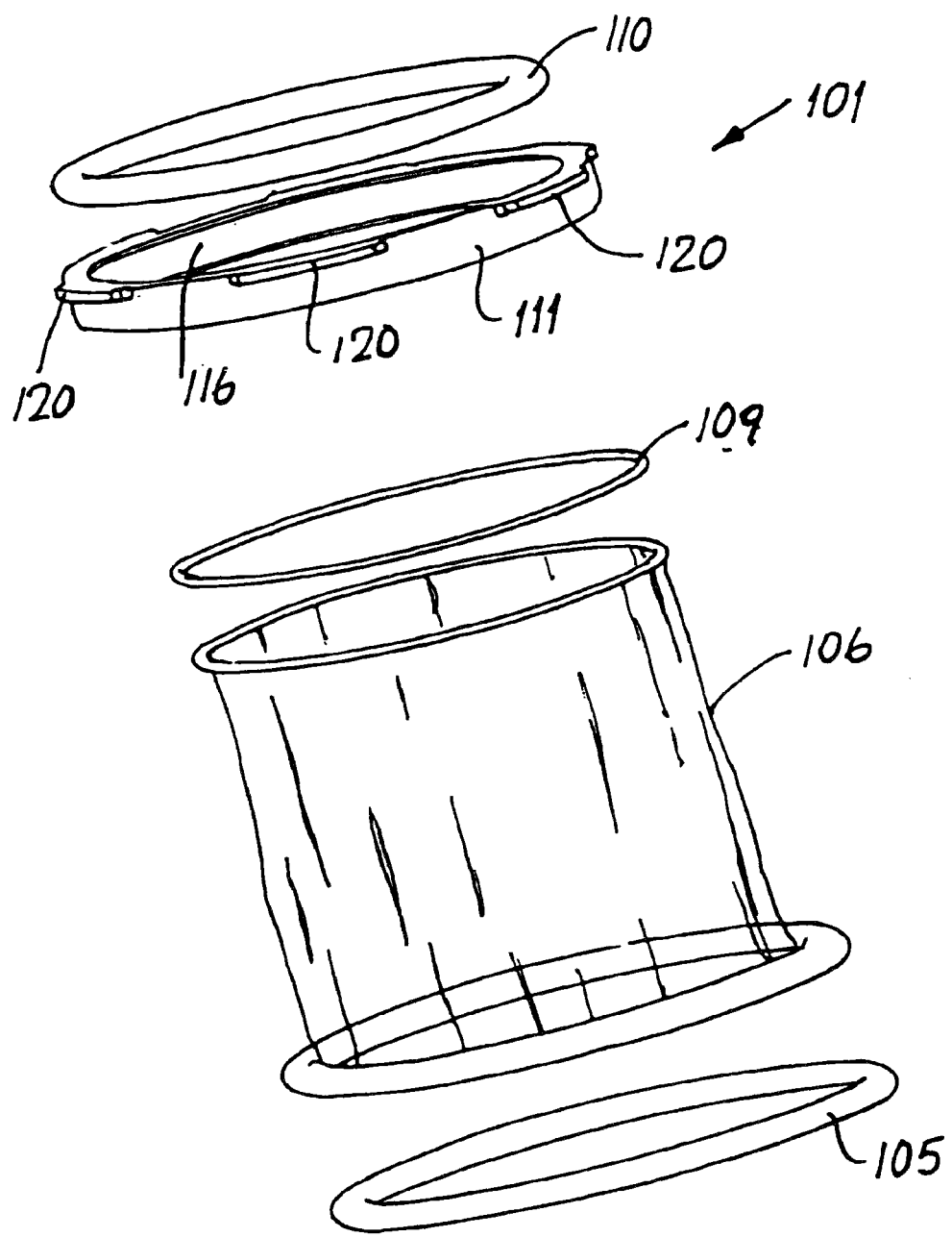
FIG. 1 is an exploded view of a wound retractor according to the invention.
Figure 2:
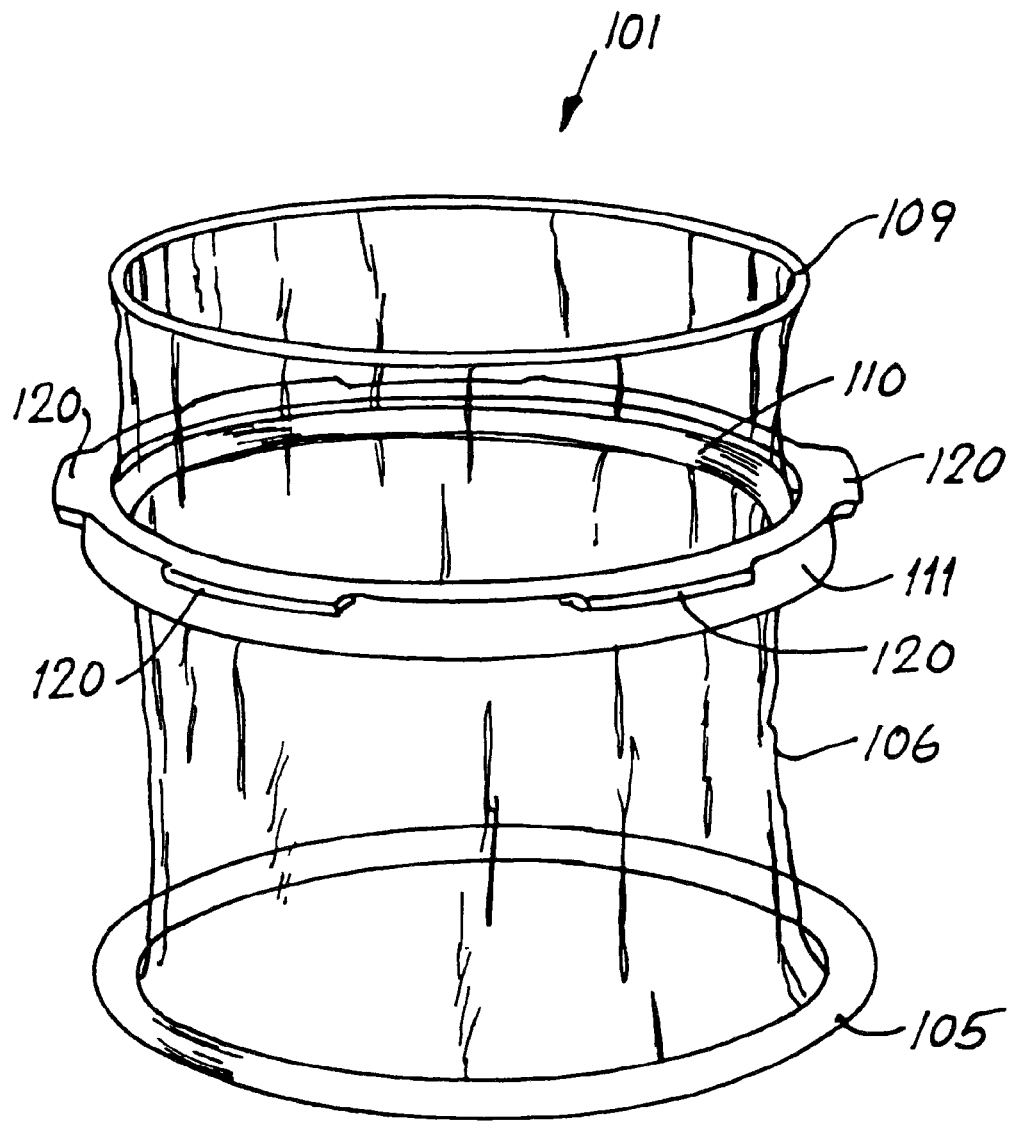
FIG. 2 is a perspective view of the retractor of FIG. 1 assembled.

The retractor 101 also includes a proximal reinforcing means for engagement with the anchor formations 120, and in this case the reinforcing means is provided by a resilient outer O-ring 109 of a material which is flexible relative to the inner O-ring 105. The outer O-ring 109 is attached to the proximal end of the sleeve 106, the rings 105, 109 helping to maintain the open shape of the sleeve 106 at its extremities (FIG. 2).

Figure 5:
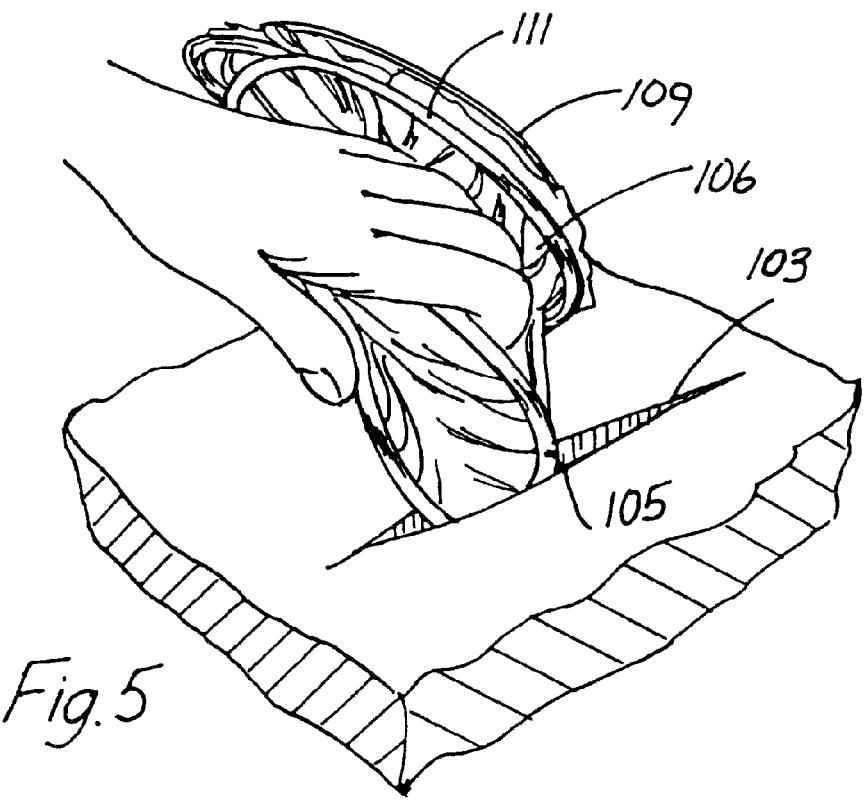
FIG. 5 is a perspective view illustrating insertion of part of the retractor of FIG. 2 into the wound opening.
Figure 6:
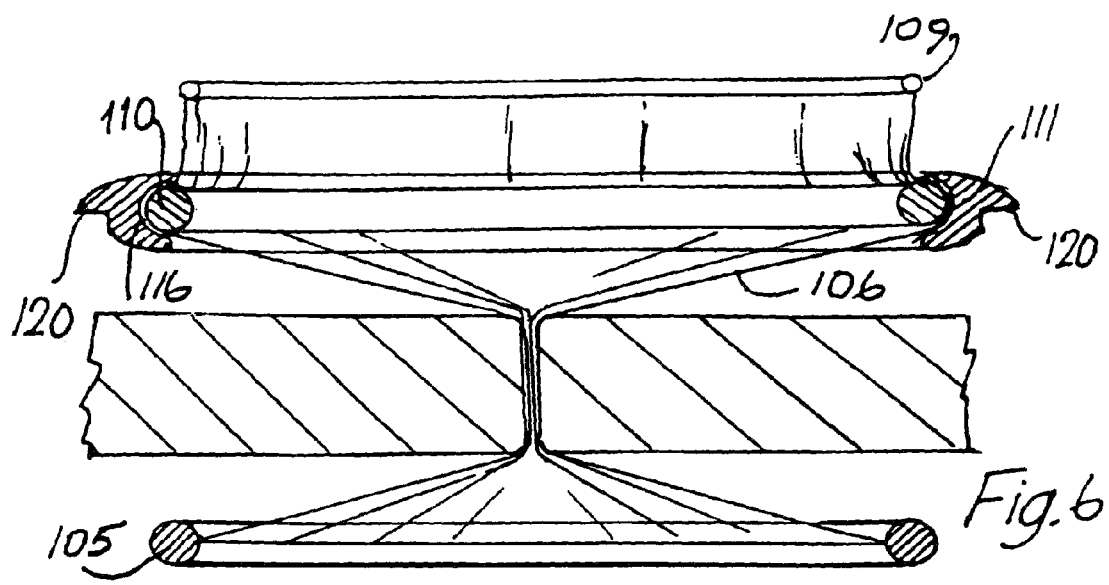
FIG. 6 is a side cross sectional view of the retractor of FIG. 2 after insertion.
Figure 7:
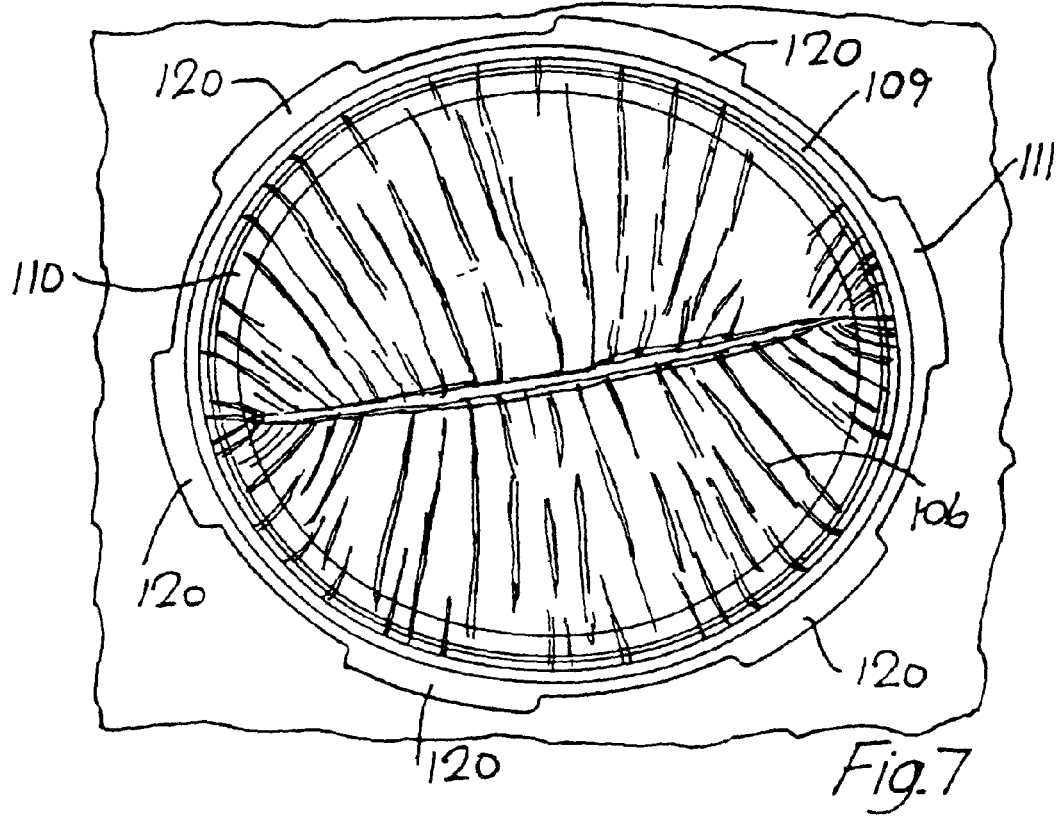
FIG. 7 is a plan view of the retractor of FIG. 2 after insertion.

In use the inner O-ring 105 and the sleeve 106 are squeezed into the insertion configuration for insertion of the inner O-ring 105 into the wound opening 103 (FIG. 5). The inner O-ring 105 is of a polymeric material which facilitates scrunching up of the inner O-ring 105 into a low-profile, elongate shape, as illustrated in FIG. 5, to facilitate case of use. On release of the inner O-ring 105, the resilient O-ring 105 returns to its normal 0-shape overlapping an inner edge of the wound opening 103 to safely anchor the retractor 101 in the wound, as illustrated in FIG. 6. As may be seen from FIGS. 6 and 7, after insertion of the inner O-ring 105, the wound opening 103 is substantially closed and the sleeve 106 is in a wrinkled compressed configuration.

Figure 8A:
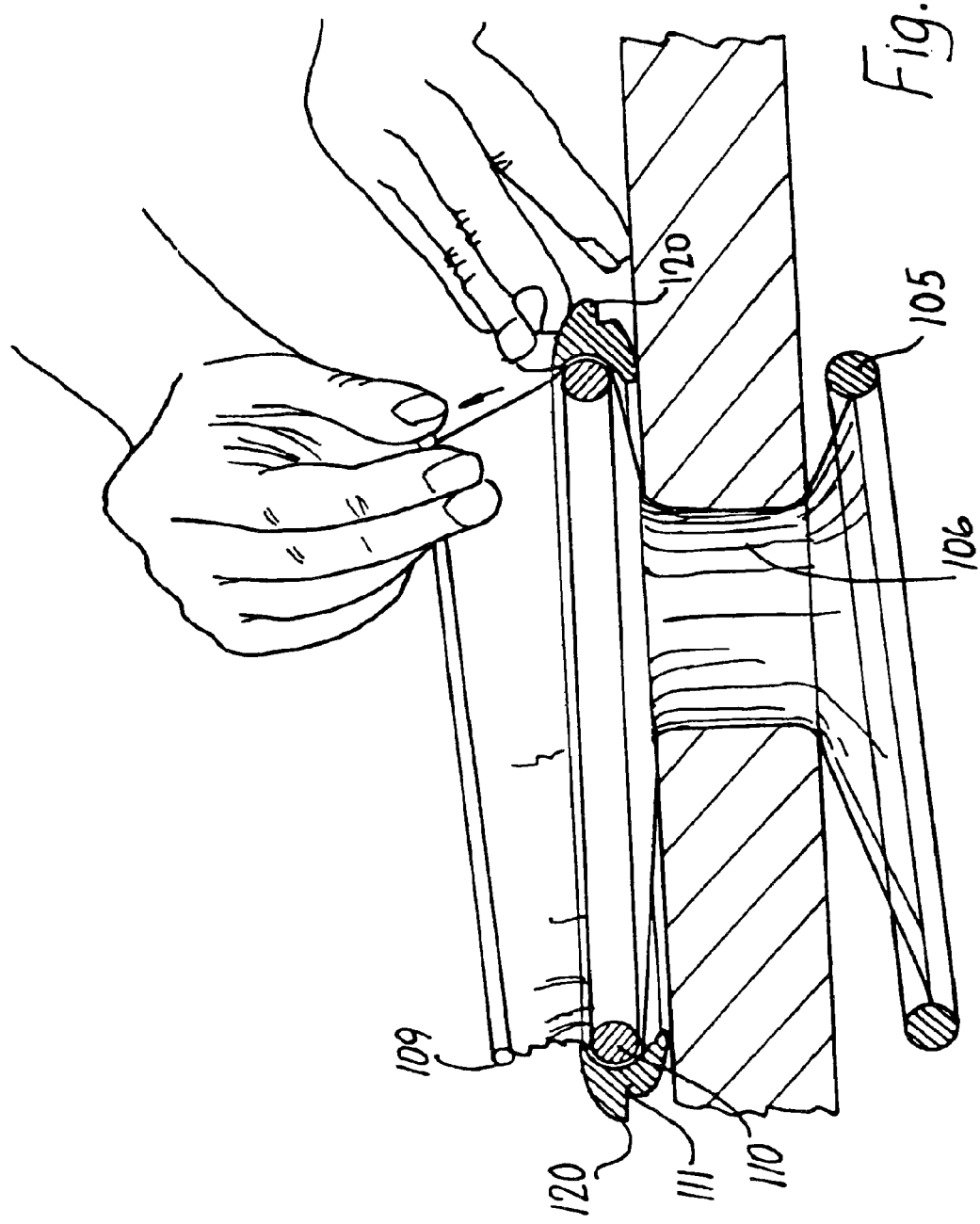

The sleeve 106 is then pulled while pushing the ring parts 110, 111 against the tissue surrounding the wound opening 103, as illustrated in FIG. 8(a), to shorten the axial extent of the sleeve 106 and thereby bias the wound engaging portion into the retracting configuration to retract laterally the right-hand side (as viewed in FIG. 8(a)) of the wound opening 103. The right-hand side of the outer O-ring 109 is hooked around the formations 120 to maintain the right-hand side of the wound opening 103 retracted (FIG. 8(b)). The left-hand side of the sleeve 106 is then pulled while pushing the ring parts 110, 111 to retract laterally the left-hand side of the wound opening 103, as illustrated in FIG. 8(b). The left-hand side of the outer O-ring 109 is then hooked around the formations 120 to maintain the entire wound opening 103 fully retracted, as illustrated in FIGS. 9 and 10.

The separate formations 120 and the configuration of the wound retractor 101 generally allow the sleeve 106 to be readily manipulated locally as illustrated in FIGS. 8(a) and 8(b) to provide an optimised retraction, force. Thus, the manipulation is not simply limited to a single vertical axis but can be carried out in several different directions by pulling of the sleeve 106, and localised hooking of the outer O-ring 109 to the appropriate formation 120. In this way the retractor can be tailored to a particular application.

Figure 13:
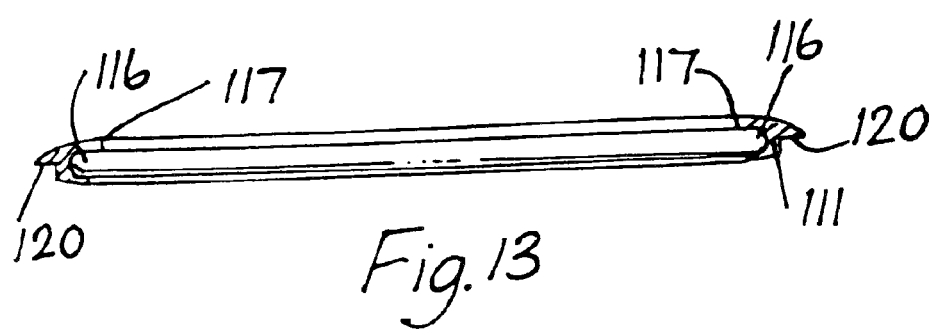
FIG. 13 is a cross sectional view along the line A-A in FIG. 11.

The recess 116 against which the sleeve 106 is slidably retained by the inner ring part 110 is C-shaped with an extended upper lip 117, as may be seen in FIG. 13. The upper lip 117 maintains the inner ring part 110 safely within the recess 116 regardless of the pulling direction or tensile pulling force exerted on the sleeve 106. It is preferable to pull the sleeve 106 in a non-vertical direction and to perform localised hooking of the outer O-ring 109, and the extended upper lip 117 encourages non-vertical pulling of the sleeve 106.

Figure 9:
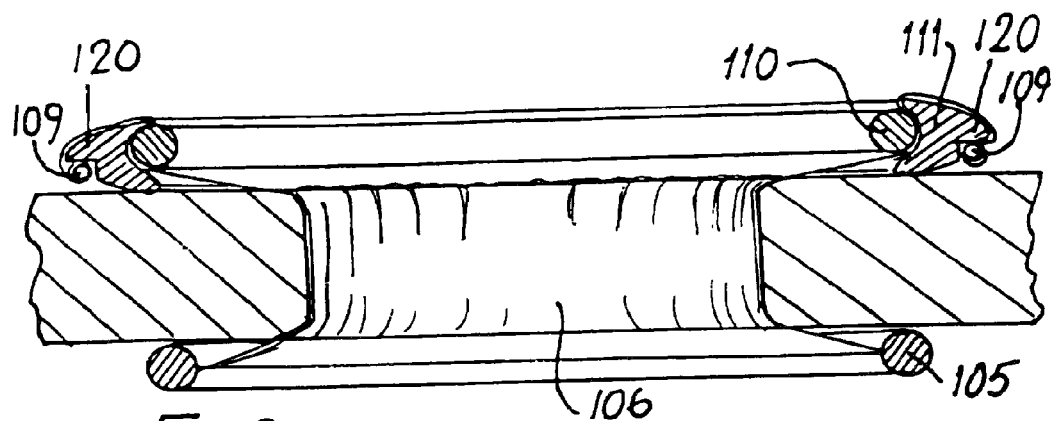
FIG. 9 is a side cross sectional view of the retractor of FIG. 2 after lateral retraction of the wound opening.
Figure 10:
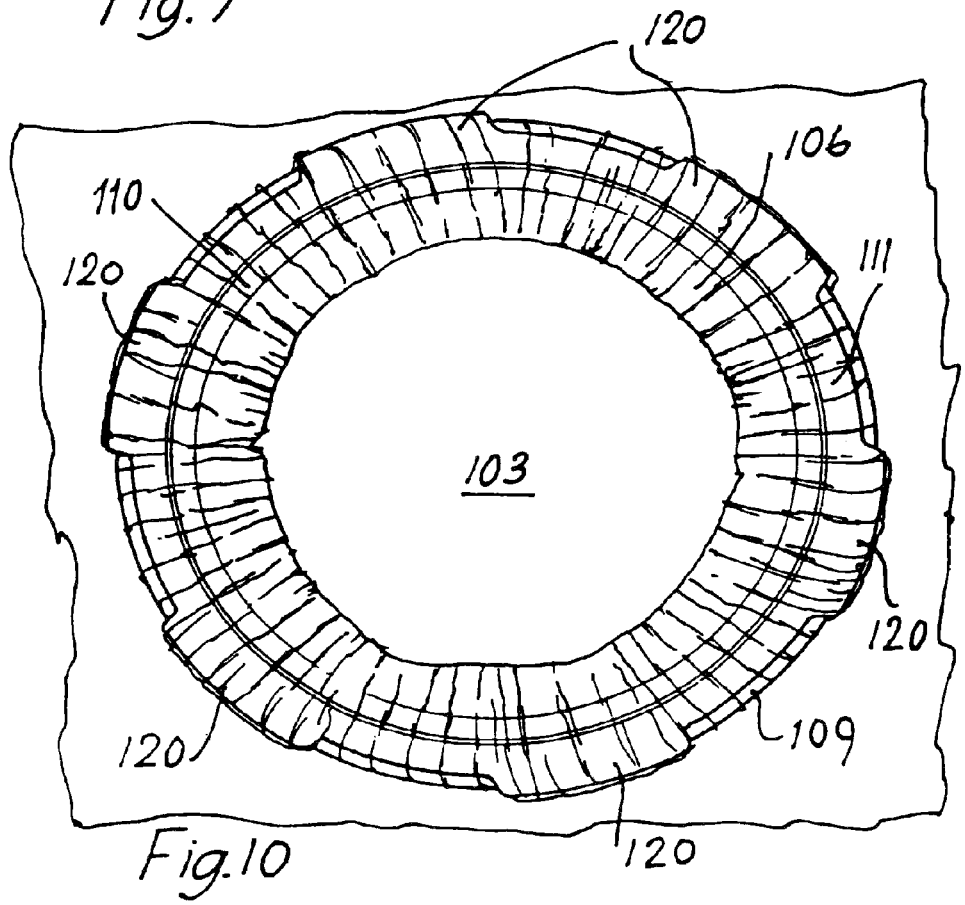
FIG. 10 is a plan view of the retractor of FIG. 2 after lateral retraction of the wound opening.
Figure 11:
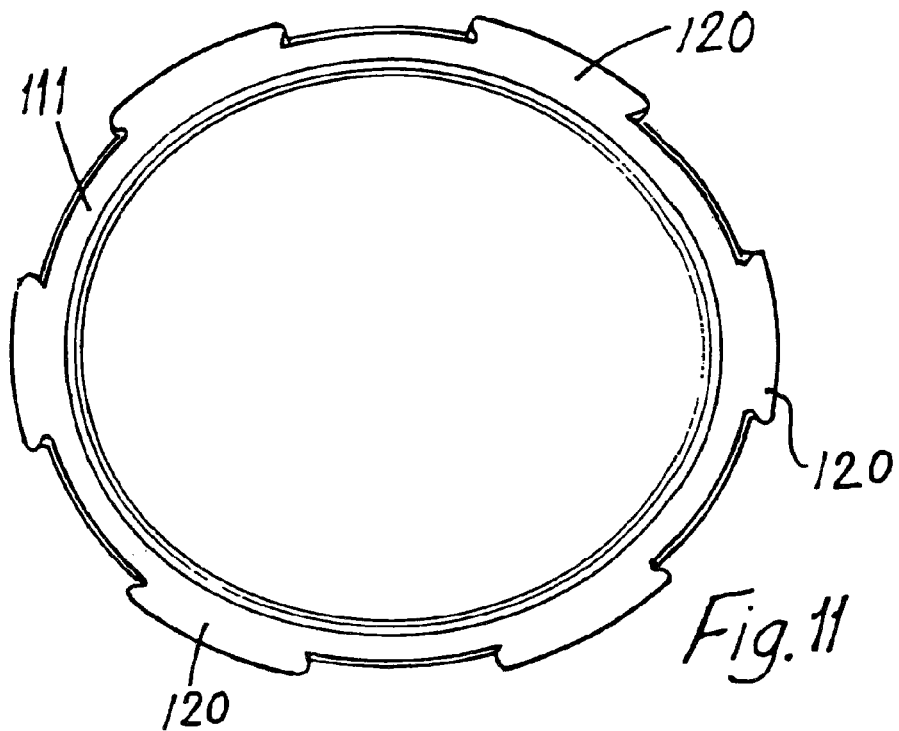
FIG. 11 is a plan view of a part of a guide means of the retractor of FIG. 2.
Figure 12:
FIG. 12 is a side view of the part of FIG. 11.

The elastomeric sleeve 106 lines the side of the retracted wound opening 103, as illustrated in FIG. 9, and thus acts both as a means of wound retraction and wound protection.

The surgical wound retractor is of simple construction, is easy to use and can be manufactured inexpensively to provide a disposable unit.

Figure 14:
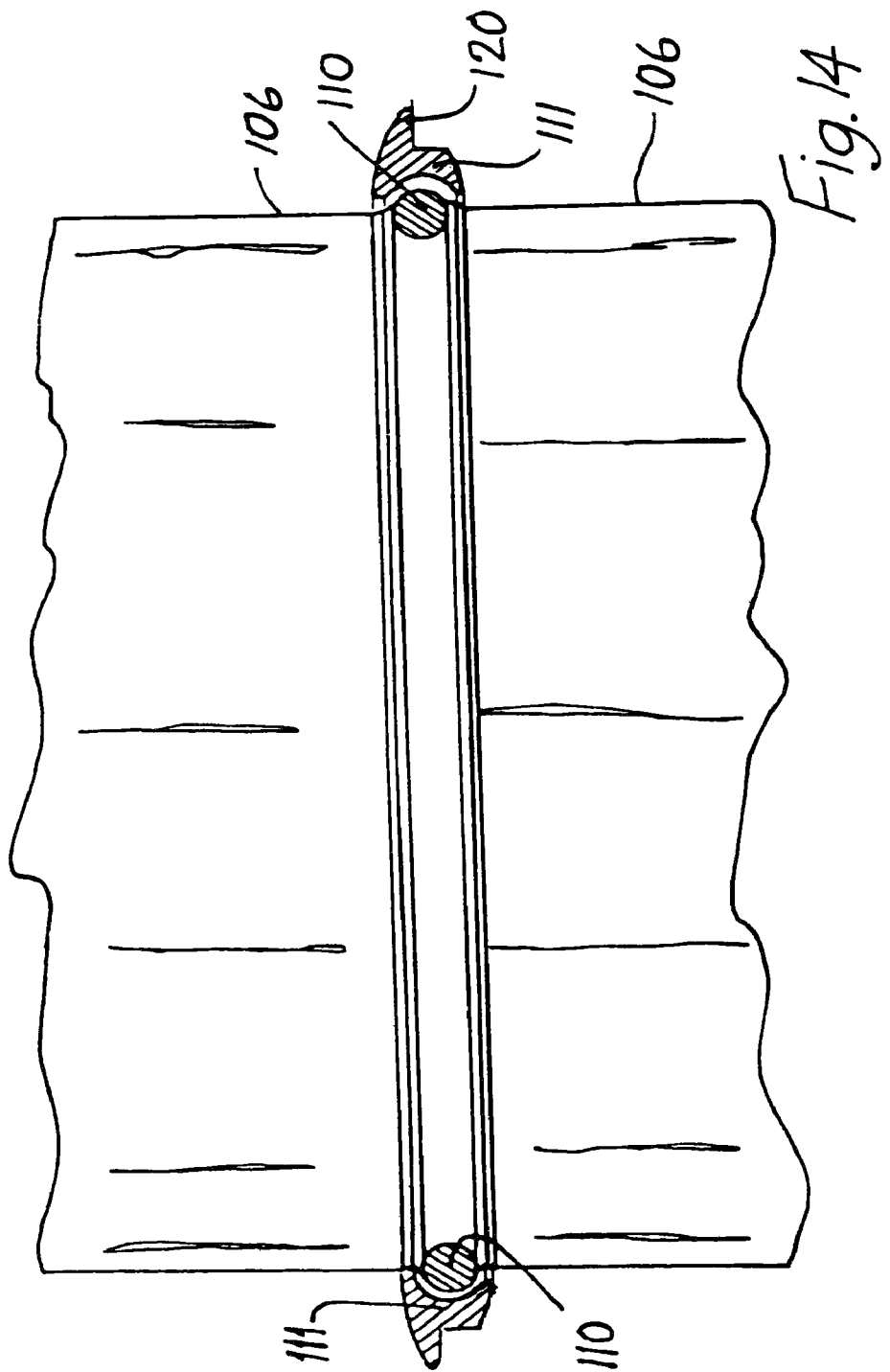
FIG. 14 is a cross sectional view of part of another wound retractor according to the invention.
Figure 15:
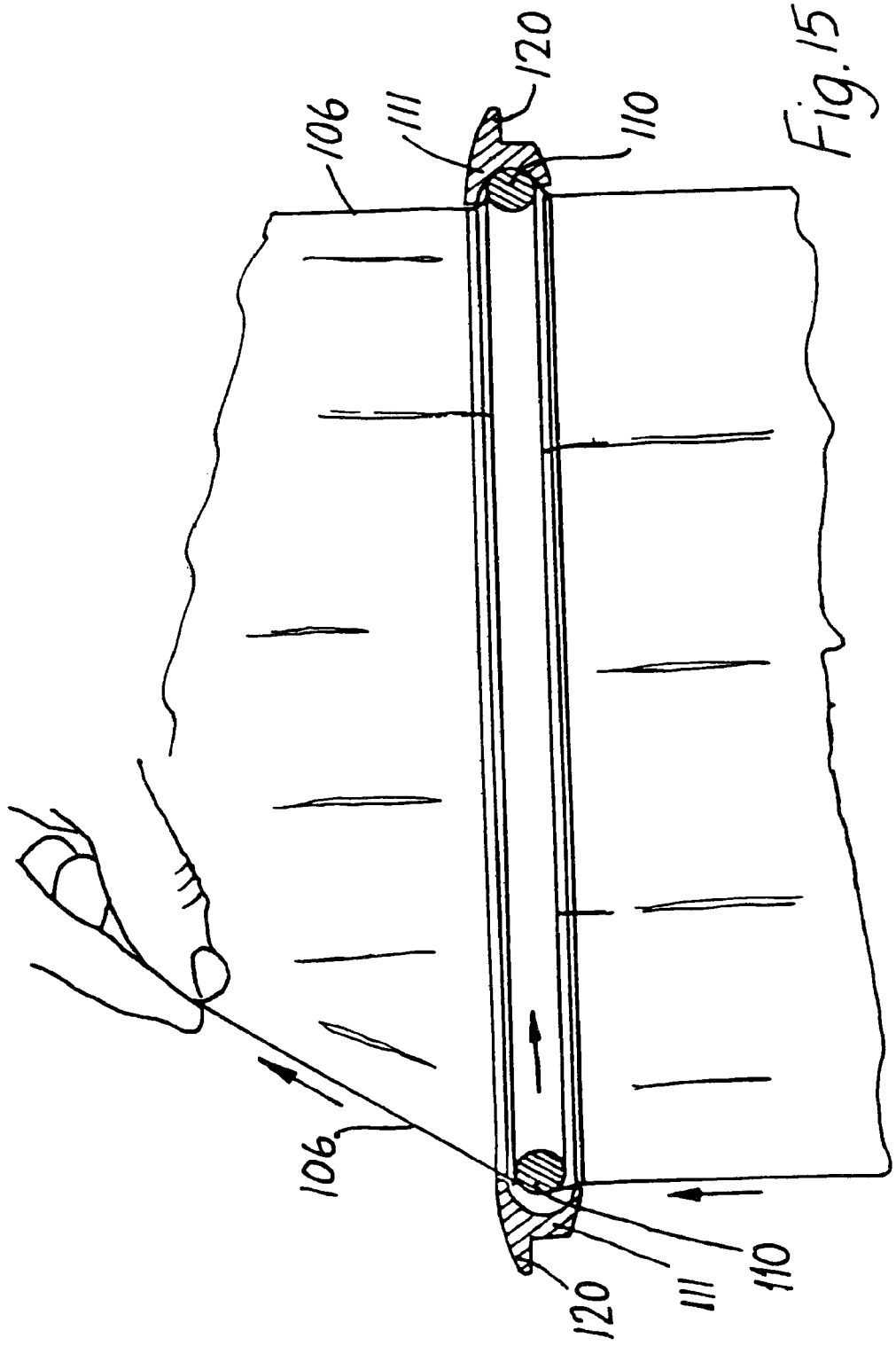
FIG. 15 is a cross sectional view of the retractor of FIG. 14, in use.
Figure 16:
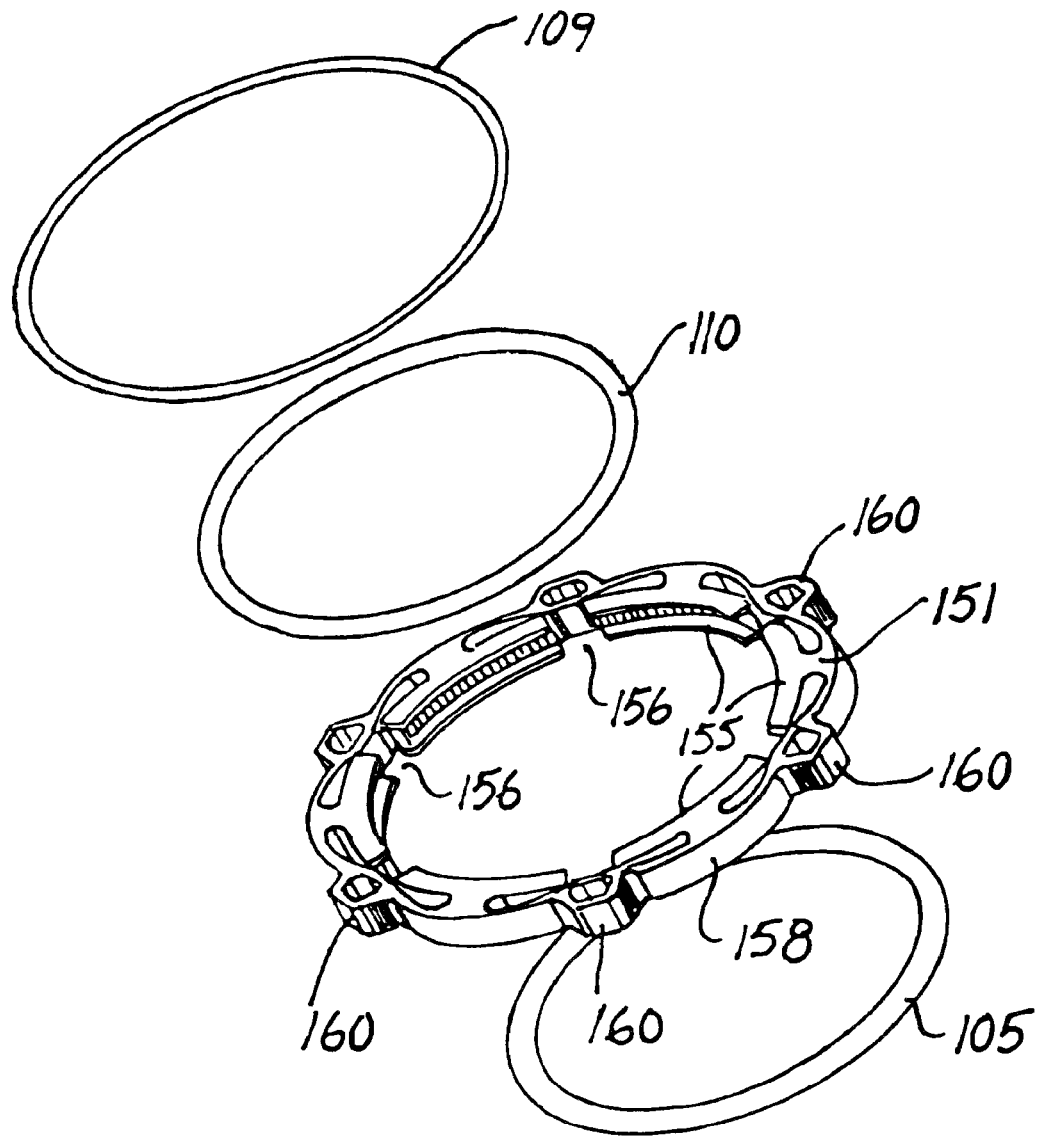
FIG. 16 is an exploded view of parts of another wound retractor according to the invention.
Figure 17:
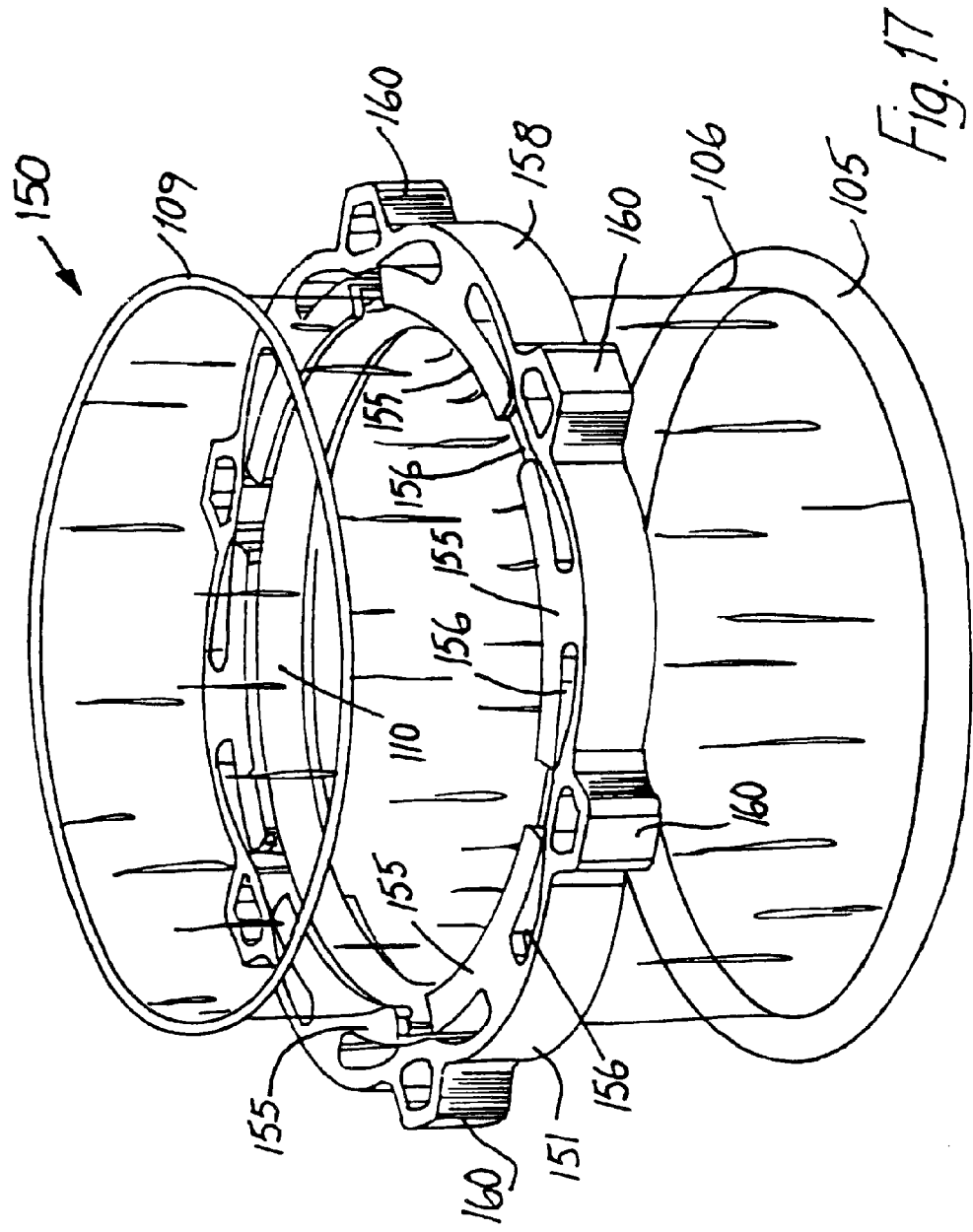
FIG. 17 is a perspective view of the wound retractor of FIG. 16 assembled.
Figure 18:
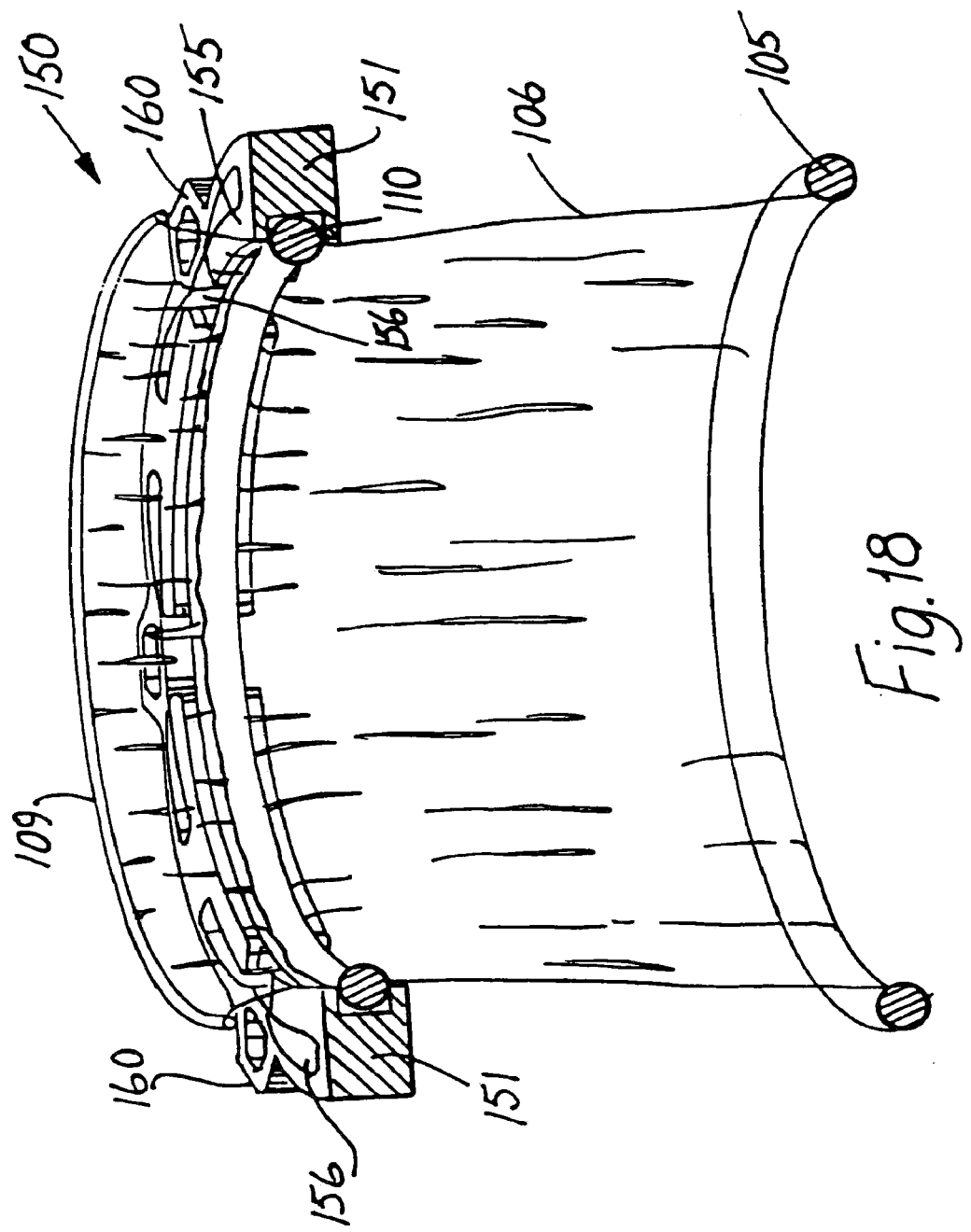
FIGS. 18 and 19 are perspective cut-away views of the retractor of FIG. 17 in different positions.
Figure 19:
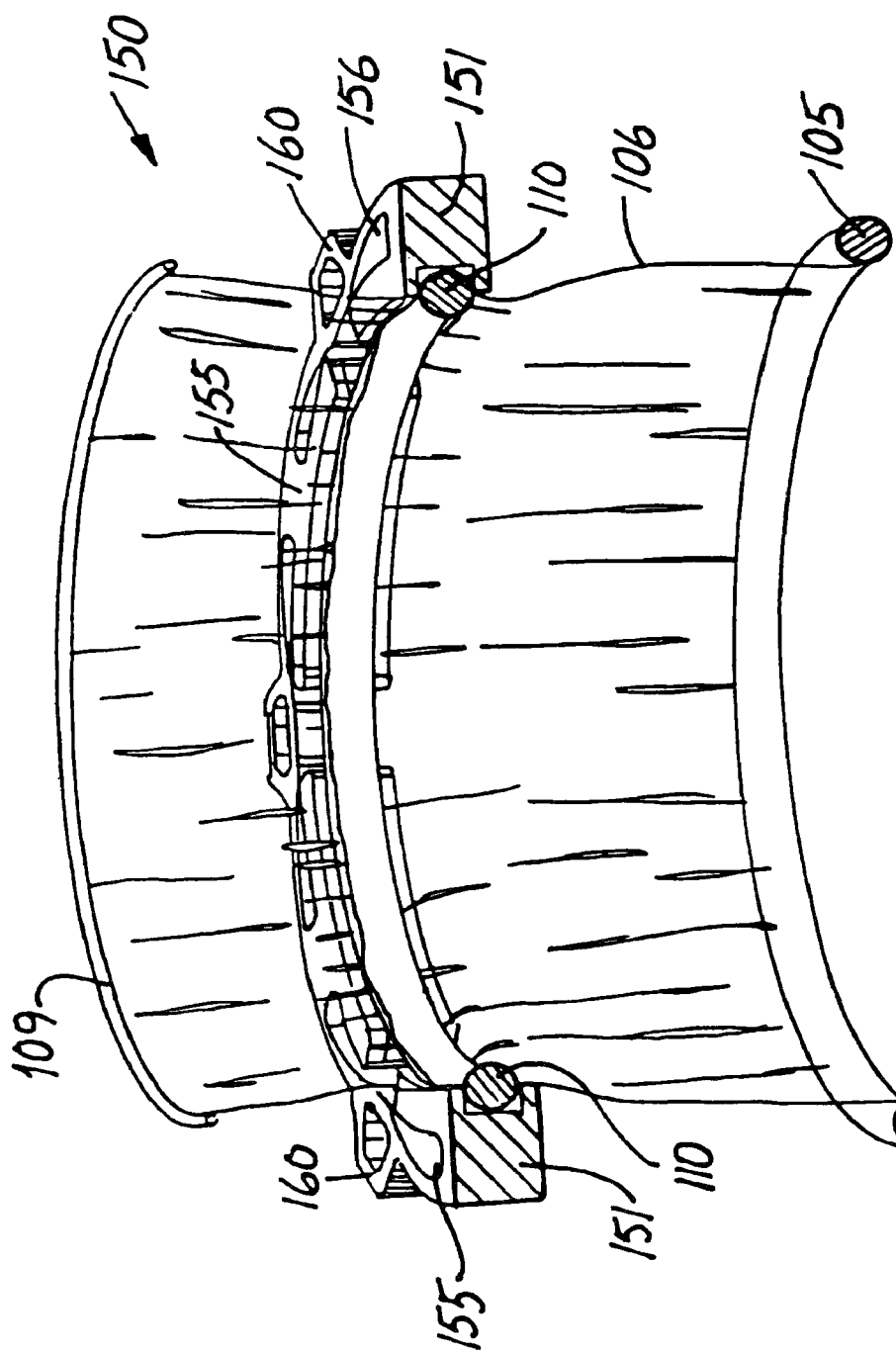

A single wound retractor according to the invention may be used for a wide range of incision sizes and to achieve a range of different localised retraction forces which are required to accommodate the incision, the patient anatomy and the surgical procedure to be performed. In the retractor of FIGS. 1 to 10 the sleeve 106 is a relatively tight fit between the outer and inner guide ring parts 110,111. It is also possible to configure the outer and inner ring parts 110, 111 so that the inner ring part 110 is a relatively looser fit in the outer part 111. In this case the guide means comprises an outer ring part or other annular shape within which slides a second component. The second component is of the same annular shape as the outer ring part but with a lesser diameter and has an exterior compartmental recess designed so that the outer ring pan fits loosely around the second component and both can easily slide relative to each other. The components fit loosely together so that an elastomeric sleeve can fit in the gap between them and slide therein. Such an arrangement is illustrated in FIGS. 14 and 15. On pulling of a local area of the sleeve i06 as indicated in FIG. 15 the inner ring part 110 moves to an appropriate side clamping the sleeve 106 at that opposite side while allowing local manipulation of the gripped section of sleeve allowing the local retraction force at the gripped side to be optimised prior to anchoring of the sleeve at that side. This procedure may be repeated at other local regions of the sleeve 106.

Referring to FIGS. 16 to 23 there is illustrated another wound retractor 150 according to the invention which is similar to the wound retractor 101 described with reference to FIGS. 1 to 13 and like parts are assigned the same reference numerals in FIGS. 16 to 23.

In this case the guide means comprises the inner ring part 110 and an outer PTFE ring part 151 configured so that the outer ring part 151 engages the inner ring part 110 at a plurality of discrete points circumferentially spaced around the outer ring part 151 to clamp the sleeve 106 between the inner and outer ring parts 110, 151 at each discrete point. The outer ring part 151 comprises a plurality of interconnected segments 155 circumferentially spaced around the outer ring part 151 which press on the inner ring part 110 to clamp the sleeve 106 and are independently movable to facilitate localised release of the sleeve 106 for adjustment of the retraction force. Cut-out T-slots 156 are provided between the segments 155 and a main body 158 of the outer ring part 151, and handles 160 project radially outwardly of the main body 158 of the outer ring part 151 intermediate the segments 155.

In use, adjacent handles 160 are manually gripped as illustrated in FIG. 20 to apply a release force in the direction of arrows A which in turn pulls the local segment 155 in the direction of arrow B from a rest position damping the sleeve 106 (FIGS. 20 and 21) to a release position (FIGS. 22 and 23) in which the sleeve 106 is readily pulled and manipulated locally. By releasing the clamp between the inner ring part 110 and the segment 155 the elastomeric sleeve 106 in readily slid from one position to another. This arrangement is particularly advantageous to facilitate local manipulation of the retraction force.

In general, the wound retractor 150 according to the invention is employed by inserting the inner O-ring 105 into a wound opening 103 and pulling the sleeve 106 so that the inner O-ring 105 lies flat against the interior anatomical surface. The inner O-ring 105 anchors the retractor 150 in the wound and prevents the elastomeric sleeve 106 from slipping out of the wound opening 103. The guide means clamp is then released by squeezing handles 160 and the ring parts 110, 151 are slid down the elastomeric sleeve 106 until they come into contact with the exterior anatomical surface. Retraction is achieved by pulling the sleeve 106 to shorten the distance between the inner O-ring 105 and the ring parts 110, 151 and thereby displace the elastomeric sleeve 106 laterally and with it the margins of the wound opening 103. The elastomeric sleeve 106 is anchored to maintain retraction of the wound opening 103 by releasing the handles 160 of the outer ring part 151 to clamp the sleeve 106.

Figure 24:
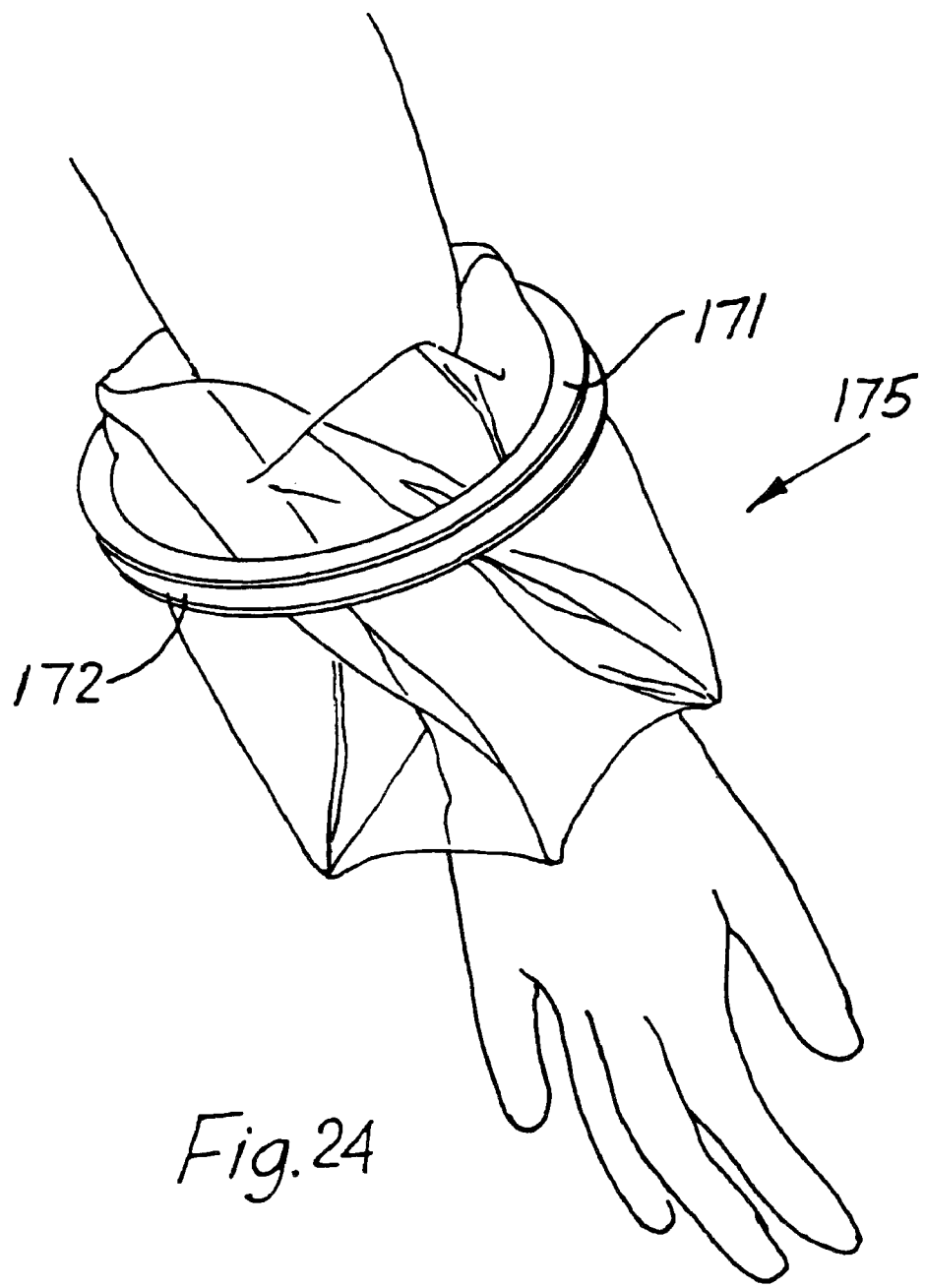
FIG. 24 is a perspective view of a hand access device for use with a wound retractor according to the invention.
Figure 25:
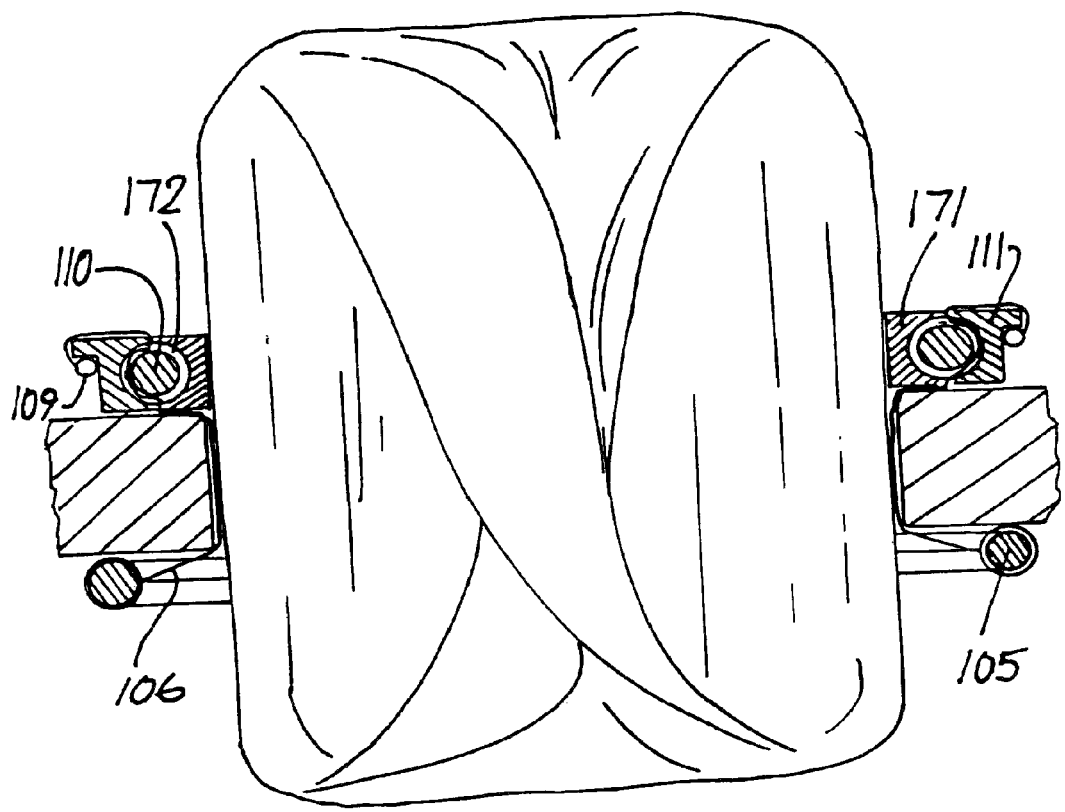
FIG. 25 is a side cross sectional view of the retractor of FIG. 2 with the hand access device of FIG. 24 in position.
Figure 26:
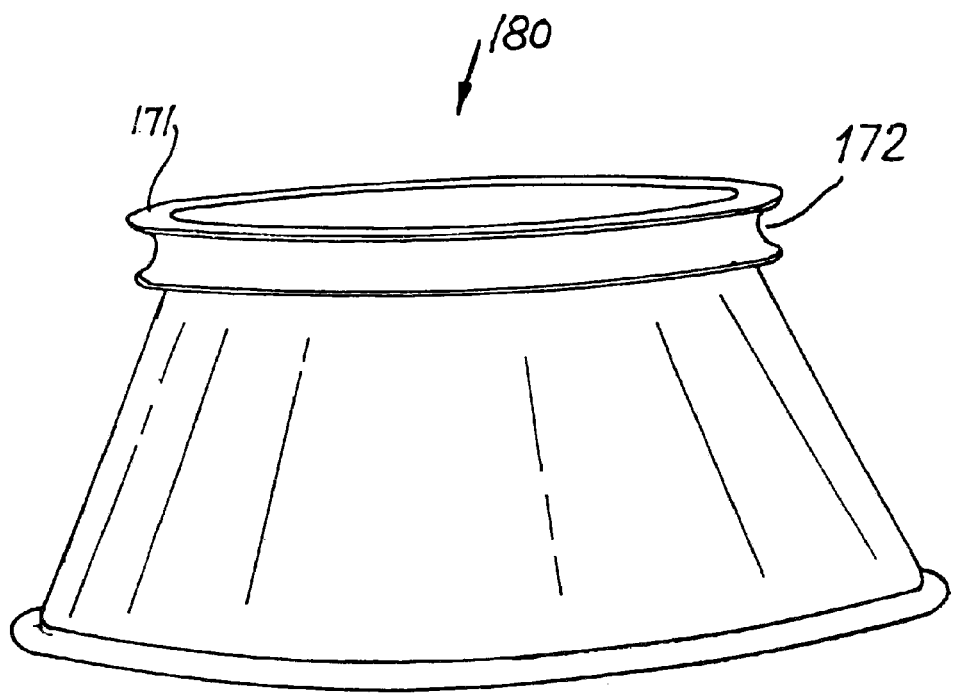
FIG. 26 is a perspective view of a drape for use with a wound retractor according to the invention.
Figure 27:
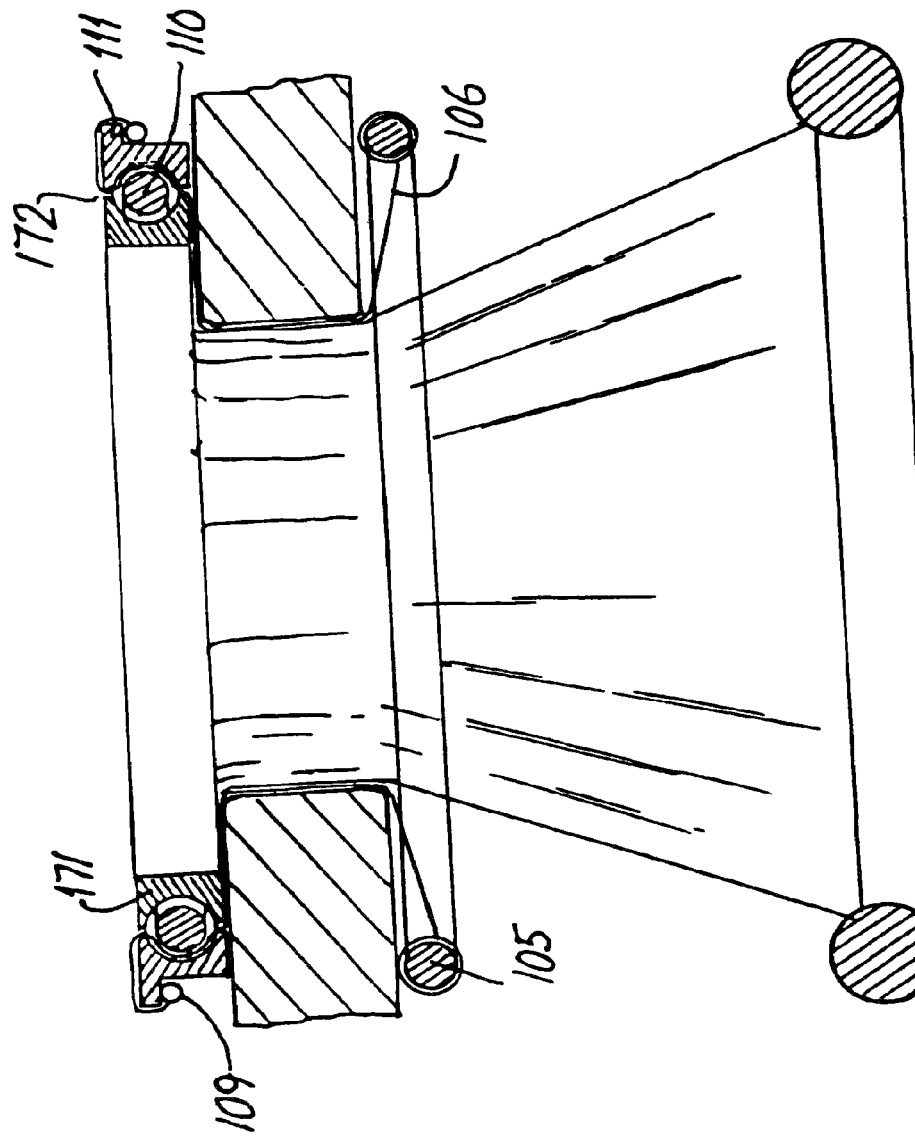
FIG. 27 is a side cross sectional view of the retractor of FIG. 2 with the drape of FIG. 26 in position.
Figure 28:
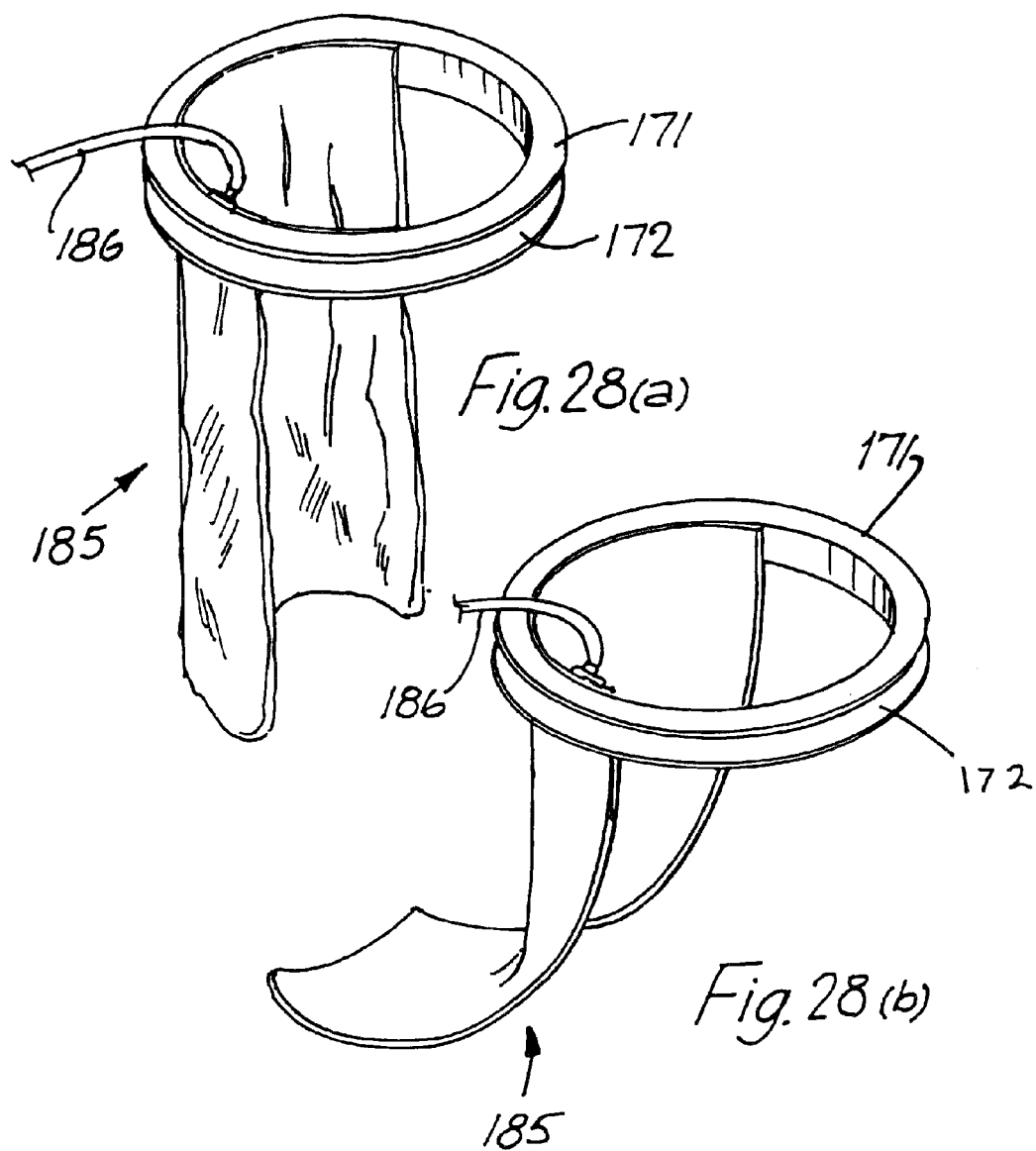
FIG. 28(a) is a perspective view of a form retaining device in a pliable state for use with a wound retractor according to the invention.
FIG. 28(b) is a perspective view of the form retaining device of FIG. 28(a) in a stiff state.
Figure 29:
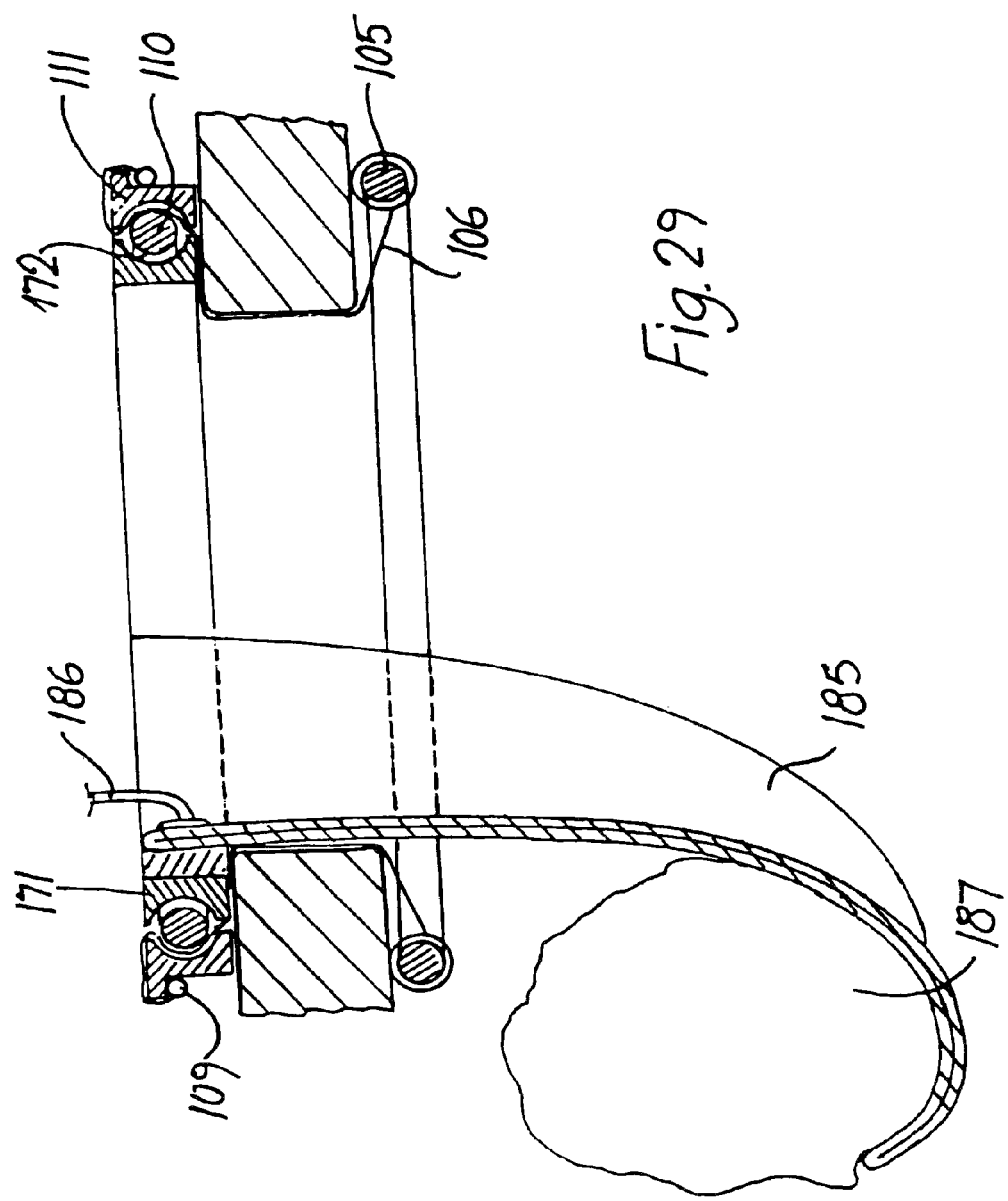
FIG. 29 is a side cross sectional view of the retractor of FIG. 2 with the stiffened form retaining device of FIG. 28(b) in position.

The wound retractors according to the invention also provides a platform on which a wide range of devices may be mounted. In one case the platform is provided by an inner projection part of the inner ring part 110 on which a ring part 171 with a complementary recess 172 may be easily fitted somewhat in the manner of a snap-type engagement. Various devices may be provided with such a ring part 171. For example, as illustrated in FIGS. 24 and 25 the device may be a hand access device 175 for use in laparoscopic surgery. Alternatively the device may be a drape 180 (FIGS. 26 and 27) or a form retaining device 185 which is manipulated to the form of, for example, an organ 187 to be held back and from which air is then evacuated along an evacuation line 186 to retain the desired organ holding configuration (FIGS. 28 and 29).

Figure 30:
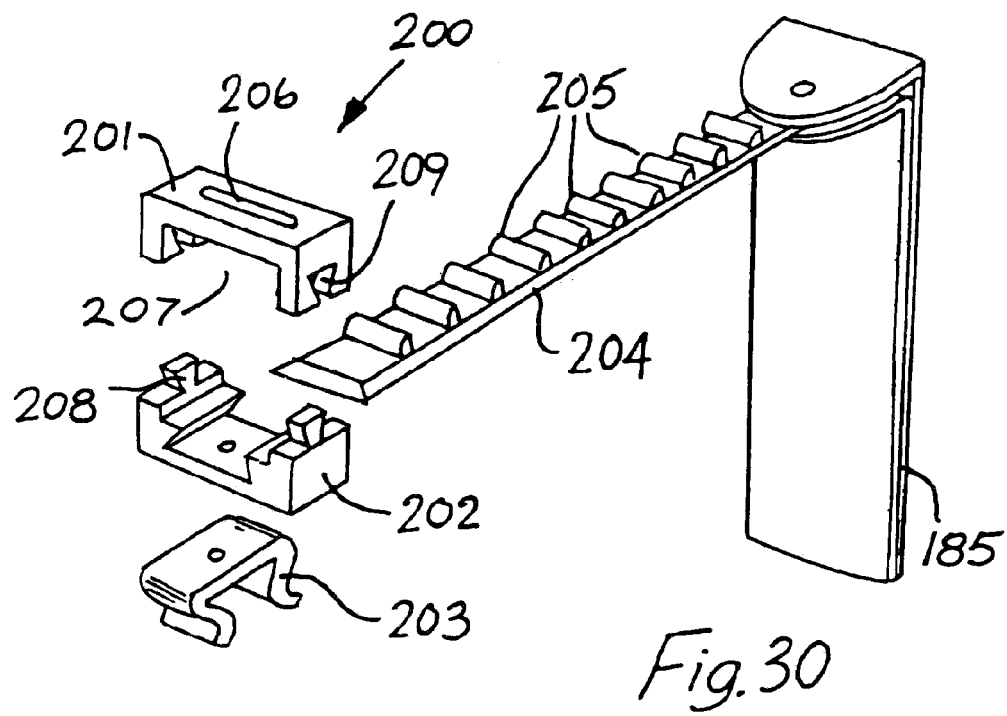
FIG. 30 is an exploded view of the form retaining device of FIG. 28 and a clamp.
Figure 31:
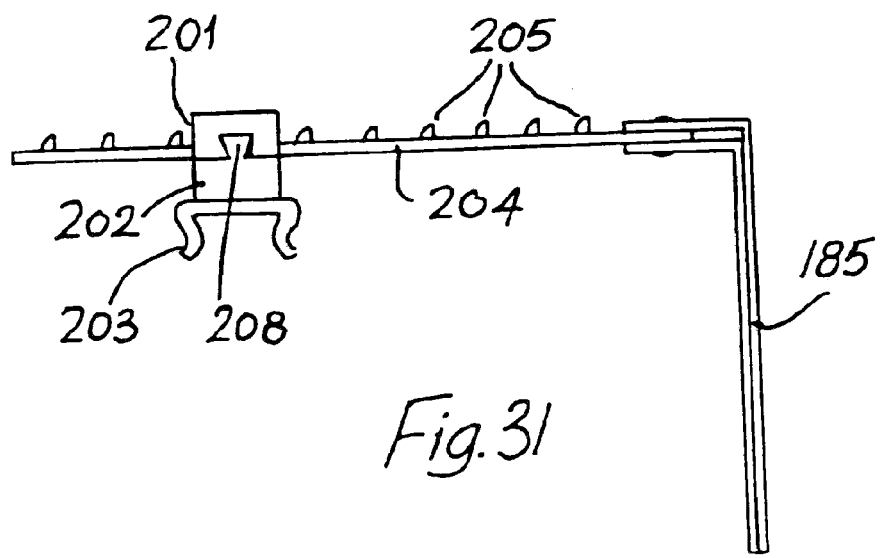
FIG. 31 is a side view of the form retaining device of FIG. 28 and the clamp of FIG. 31.
Figure 32:
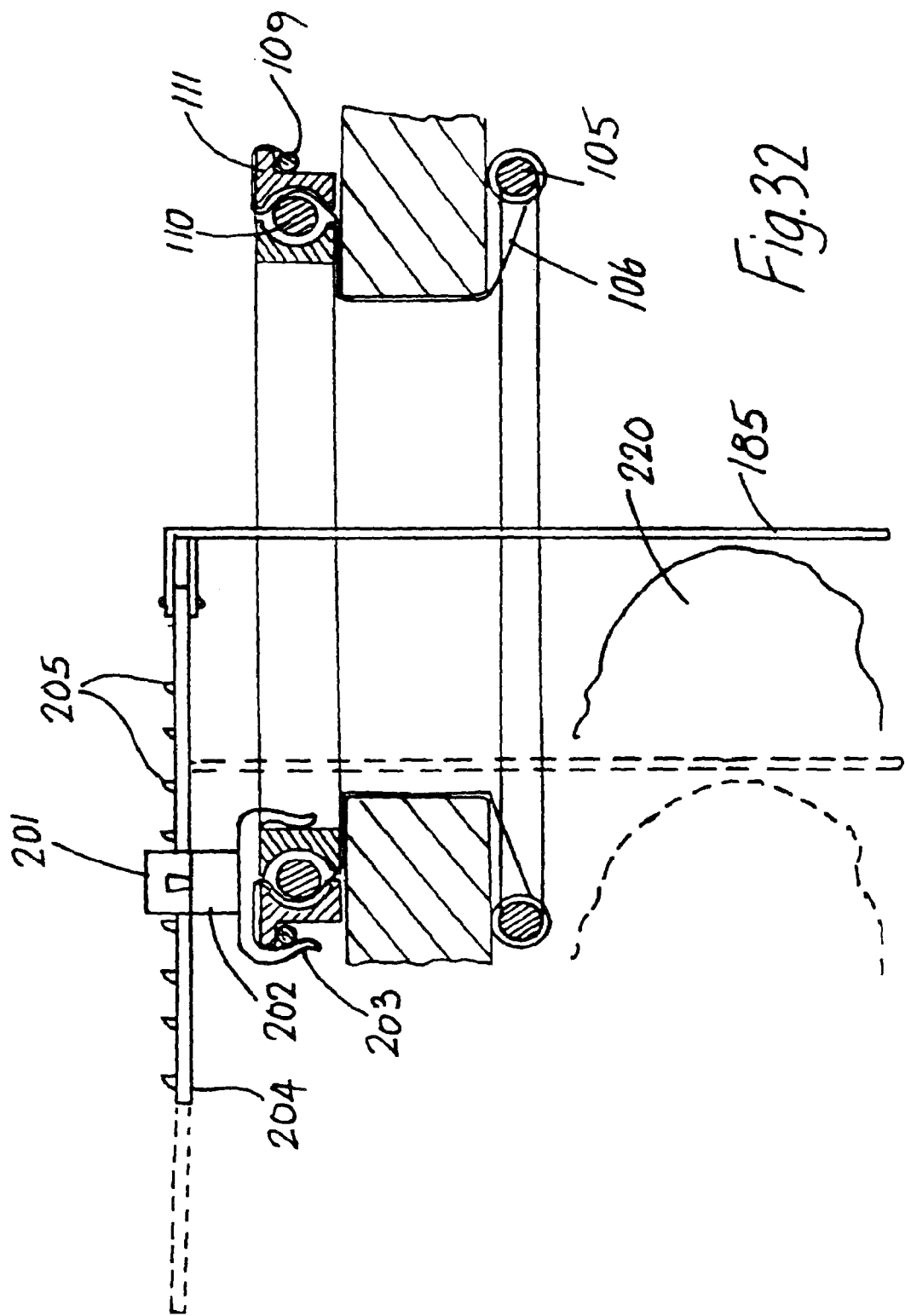
FIG. 32 is a side cross sectional view of the retractor of FIG. 2 with the form retaining device of FIG. 28 and the clamp of FIG. 30 in position.

The platform may alternatively be provided by a clamp 200 as illustrated in FIGS. 30 to 32. The clamp 200 comprises an upper jaw 201, a lower jaw 202, a clip 203 and an arm 204.

The clamp 200 is assembled by screwing the clip 203 to the base of the lower jaw 202, sliding the upper jaw 201 over the lower jaw 202 to engage the male projecting parts 208 within the corresponding female recesses 209 and extending the arm 204 through the open mouth 207 between the upper and lower jaws 201, 202. A plurality of teeth 205 are provided on the arm 204, the teeth 205 being sized to project upwardly through a recess 206 in the upper jaw 201 when the arm 204 is within the open mouth 207. The teeth 205, as shown more clearly in FIG. 31, are shaped such that the arm 204 may be pulled back through the open mouth 207 in a ratchet-type arrangement but cannot be pushed forward again. A suitable material for the clamp components 201, 202, 203, 204 is spring steel.

Various devices may be attached to the free end of the arm 204, such as the form retaining device 185, as illustrated in FIG. 30. In use the clip 203 is securely fixed to the wound retractor 101 by a snap-fit arrangement with the form retaining device 185 extending into the wound opening 103, as illustrated in FIG. 31. The form retaining device 185 is then ratcheted laterally across the wound opening 103 to retract, for example, an internal organ 220. The ratchet configuration of the clamp 200 and the rigidity of the form retaining device 185 ensure that the internal organ 220 is securely maintained in a desired position.

It will be appreciated that any of the embodiments of the wound retractor according to the invention may be used as a platform on which to mount other devices for use in various surgical procedures. Such devices may include: a capping device to cover the incision site or orifice; a hand-access device to allow the surgical procedure to be converted from an open procedure into a hand-assisted laparoscopic procedure; an instrument port for the insertion of instruments; a trocar for use in laparoscopic surgery; an internal organ retractor to assist in the displacement of internal structures from the operative field; or an illuminating means to deliver illumination to an area shaded from the theatre lights. It will be clear to those skilled in the art that the enhancements are not limited to the brief list mentioned here.

The wound retractor may be constructed in other annular shapes. For example the distal and proximal rings attached to the elastomeric sleeve may be oval or elliptical instead of circular.

The retractor may be used to retract and protect the margins of a natural bodily orifice such as the anus or vagina, or can be used to retract and protect the edges of a man-made stoma such as is created for tracheostomy or following gastrointestinal surgery.

The invention is not limited to the embodiments hereinbefore described which may be varied in both construction and detail.

The invention claimed is:

1. A medical device, comprising:
 a wound protector, including:
  a proximal ring,
  a distal ring, and
  a sleeve extending between the proximal ring and the distal ring, wherein the distal ring and a distal portion of the sleeve are configured for insertion into an incision, and the proximal ring and a proximal portion of the sleeve are configured for positioning outside of the incision; and
 a proximal assembly coupled to the proximal ring, the proximal assembly including:
  an outer member coupled to the proximal ring,
  an inner member, wherein at least part of the inner member is received by the outer member, and the inner member slidably engages the outer member, and
  an access portion providing a passageway through the proximal assembly.

2. The medical device of claim 1, wherein the outer member has an inner circumferential portion, the inner member has an outer circumferential portion, and the inner circumferential portion slidably engages the outer circumferential portion.

3. The medical device of claim 1, wherein one of the inner member and the outer member includes a recess, and the other of the inner member and the outer member includes a portion that protrudes into the recess.

4. The medical device of claim 1, wherein the outer member is annular.

5. The medical device of claim 1, wherein the inner member is annular.

6. The medical device of claim 1, wherein the access portion includes a cylindrical port.

7. The medical device of claim 1, wherein the access portion extends proximally from a proximal surface of the inner member.

8. The medical device of claim 7, wherein a proximal end of the access portion includes a proximal opening.

9. The medical device of claim 8, wherein the access portion extends distally from a distal surface of the inner member.

10. The medical device of claim 9, wherein a distal end of the access portion includes a distal opening.

11. The medical device of claim 1, wherein a longitudinal axis of the access portion is coaxial with a longitudinal axis of the wound protector.

12. A medical device, comprising:
 a wound protector, including:
  a proximal ring,
  a distal ring, and
  a sleeve extending between the proximal ring and the distal ring, wherein the distal ring and a distal portion of the sleeve are configured for insertion into an incision, and the proximal ring and a proximal portion of the sleeve are configured for positioning outside of the incision; and
 a proximal assembly coupled to the proximal ring, the proximal assembly including:
  a base coupled to the proximal ring, the base having a proximal surface and a distal surface, and
  an access portion configured to provide passage through the base, wherein the access portion extends proximally from the proximal surface of the base, the access portion has a proximal end with a proximal aperture, and the proximal aperture is spaced in a proximal direction from the proximal surface of the base.

13. The medical device of claim 12, wherein the access portion has a central passageway in fluid communication with the proximal aperture.

14. The medical device of claim 12, wherein the base is coupled to the proximal ring by an annular proximal receiver.

15. The medical device of claim 14, wherein the base includes one of a protrusion and a recess, the proximal receiver includes the other of the protrusion and the recess, and the protrusion is received by the recess.

16. The medical device of claim 15, wherein the protrusion and the recess are configured for snap-fit engagement.

17. The medical device of claim 12, wherein a longitudinal axis of the access portion is coaxial with a longitudinal axis of the wound protector.

18. A method of retracting and sealing an incision for laparoscopic procedures, comprising:
 making an incision in a patient;
 positioning a wound retractor system proximate the incision, the wound retractor system including:
  a distal ring,
  a proximal ring,
  a sleeve extending between the distal ring and the proximal ring and fixedly coupled to both the proximal ring and the distal ring, and
  a proximal receiver including a recess;
 inserting the distal ring through the incision such that the sleeve extends through the incision and the proximal ring is located outside of the incision;
 retracting the incision with the sleeve;
 coupling a portion of the proximal ring to the recess of the proximal receiver so that the receiver restricts movement of the proximal ring and an actual length of the sleeve between the distal ring and the proximal receiver is shortened; and
 coupling an access device to the proximal receiver.

19. The method of claim 18, wherein the coupling of the access device to the proximal receiver includes a coupling via a snap-fit engagement.

20. The method of claim 18, wherein retracting the incision includes inverting at least a portion of the sleeve prior to coupling the portion of the proximal ring to the recess of the proximal receiver.

* * * * *